(12) United States Patent
Nose et al.

(10) Patent No.: US 8,058,051 B2
(45) Date of Patent: Nov. 15, 2011

(54) **BACTERIUM BELONGING TO THE GENUS *BIFIDOBACTERIUM* AND UTILIZATION OF THE SAME**

(75) Inventors: Atsushi Nose, Minato-ku (JP); Daisuke Nozaki, Minato-ku (JP); Fumiyasu Ishikawa, Minato-ku (JP); Susumu Mizusawa, Minato-ku (JP); Ryoichi Akahoshi, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 954 days.

(21) Appl. No.: 11/996,445

(22) PCT Filed: Jul. 20, 2006

(86) PCT No.: PCT/JP2006/314369
§ 371 (c)(1),
(2), (4) Date: Jan. 22, 2008

(87) PCT Pub. No.: WO2007/010977
PCT Pub. Date: Jan. 25, 2007

(65) Prior Publication Data
US 2009/0252709 A1  Oct. 8, 2009

(30) Foreign Application Priority Data
Jul. 21, 2005  (JP) .................................. 2005-211670

(51) Int. Cl.
*C12N 1/20* (2006.01)
*A23C 9/12* (2006.01)

(52) U.S. Cl. ........................ 435/252.1; 424/93.4; 426/61

(58) Field of Classification Search ........................ None
See application file for complete search history.

(56) References Cited

U.S. PATENT DOCUMENTS

| | | | | |
|---|---|---|---|---|
| 4,870,020 A | * | 9/1989 | Sozzi | 435/252.1 |
| 5,638,660 A | * | 6/1997 | Kuo | 53/449 |
| 7,153,502 B2 | * | 12/2006 | Kimura et al. | 424/93.45 |

FOREIGN PATENT DOCUMENTS

| | | |
|---|---|---|
| EP | 1 443 105 A1 | 8/2004 |
| JP | 9 322762 | 12/1997 |
| JP | 2922013 | 4/1999 |
| JP | 11 137172 | 5/1999 |
| JP | 3261571 | 12/2001 |
| JP | 2002 335860 | 11/2002 |
| JP | 2003 250528 | 9/2003 |
| WO | 03 040350 | 5/2003 |

OTHER PUBLICATIONS

Collado et al., International Journal of Antimicrobial Agents 25 (2005) 385-391, published May 2005.*
Yamamoto, Yoshihiro, "*Bifidobacterium bifidum* YIT 4007", Tokyo Metropolitan Police Hospital, Division of Gastroenterology, et al., vol. 22, No. 11, 1994, pp. 253-256.
Wang, Kuan-Yuan et al., "Effects of ingesting *Lactobacillus*- and *Bifidobacterium*-containing yogurt in subjects with colonized *Helicobacter pylori*", The American Journal of Clinical Nutrition, 2004, pp. 737-741.
Sheu, B. S., et al., "Impact of supplement with *Lactobacillus*- and *Bifidobacterium*-containing yogurt on triple therapy for *Helicobacter pylori* eradication", Aliment Pharmacol Ther, Blackwell Science Ltd, XP-002490405, Jun. 17, 2002, pp. 1669-1675.
Miki, K. et al., "Effect of *Bifidobacterium bifidum* Fermented Mike on *Helicobacter pylori* and Serum Pepsinogen Levels in Humans", American Dairy Science Association, XP-002490406, 2007, pp. 2630-2640.
K. Hashimoto, et al., "Effect of *Bifidobacteriium bifidum* Strain Yakult-Containing Fermented Milk on *Helicobacter Pylori*-Positive Healthy Volunteers", Associate Journal of Japanese Society for Medical Use of Functional Foods, vol. 2, No. 3, pp. 203-213, Mar. 2005.

* cited by examiner

*Primary Examiner* — Irene Marx
(74) *Attorney, Agent, or Firm* — Oblon, Spivak, McClelland, Maier & Neustadt, L.L.P.

(57) ABSTRACT

It is intended to provide *Bifidobacterium bifidum* which has an effect of killing *Helicobacter pylori* and shows high survivability even in the case of being stored in a fermented milk food or drink under aerobic condition. The *Bifidobacterium bifidum* has the following characteristics: (1) having an effect of killing *Helicobacter pylori*; and (2) showing a survival rate of 10% or higher in the case of being stored in a fermented milk drink or food under aerobic condition at 10° C. for 14 days.

7 Claims, 11 Drawing Sheets

[Fig.1]
[Fig.2]
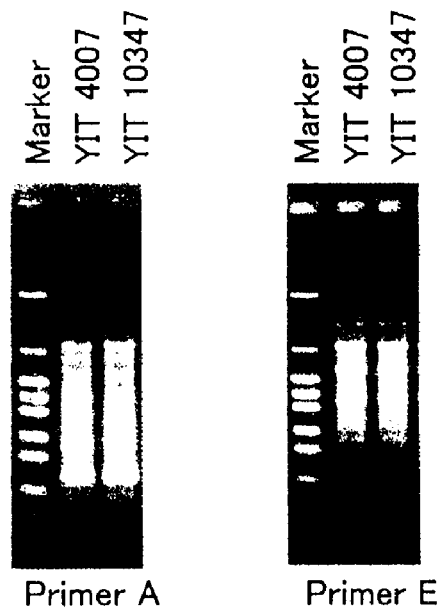

[Fig.3]
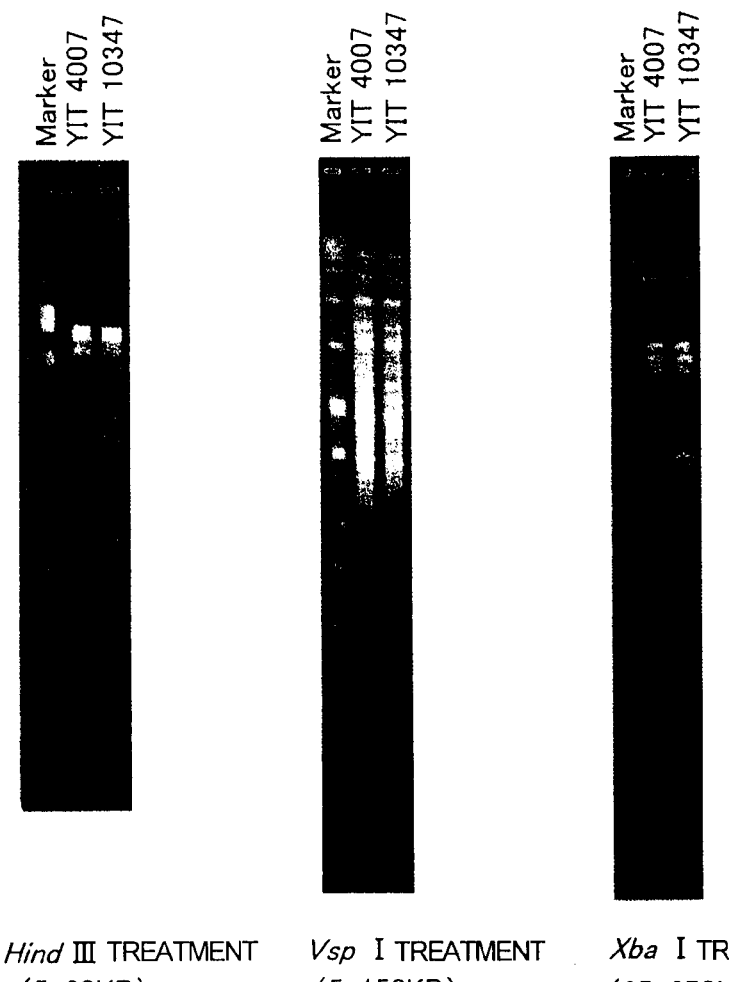

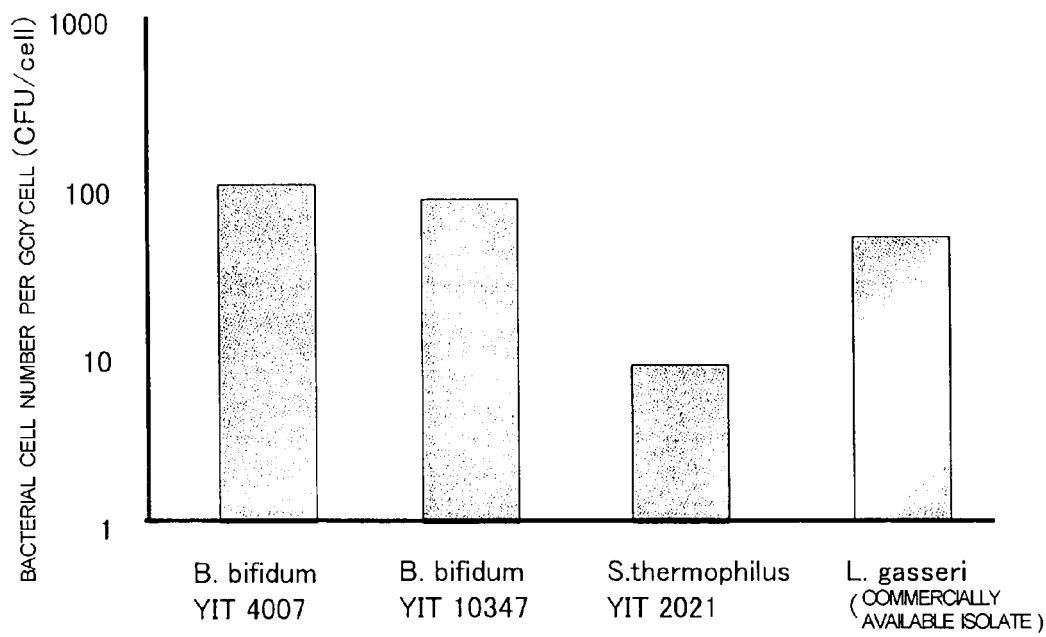
[Fig.4]
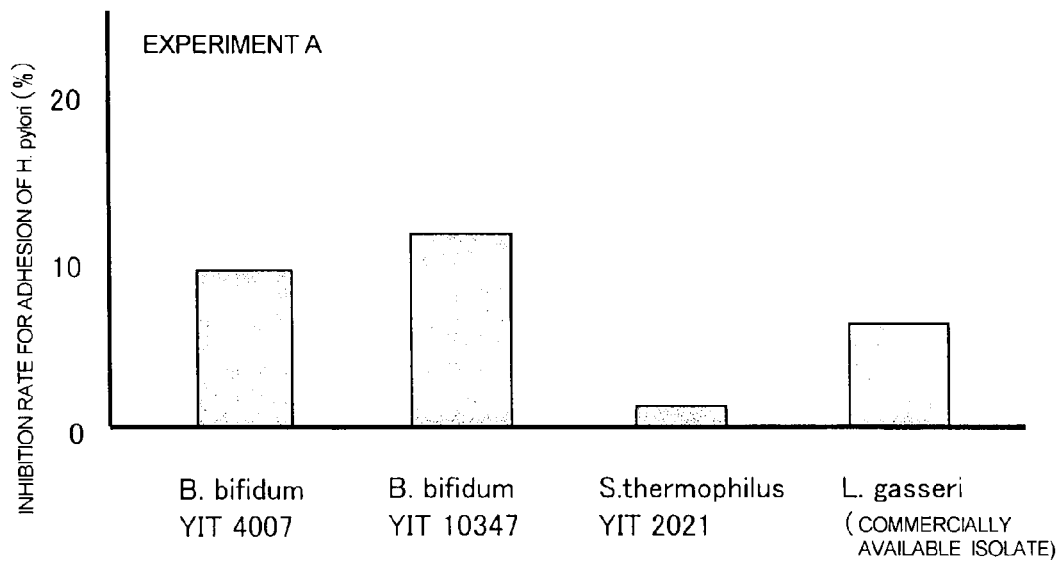
[Fig.5]

[Fig.6]
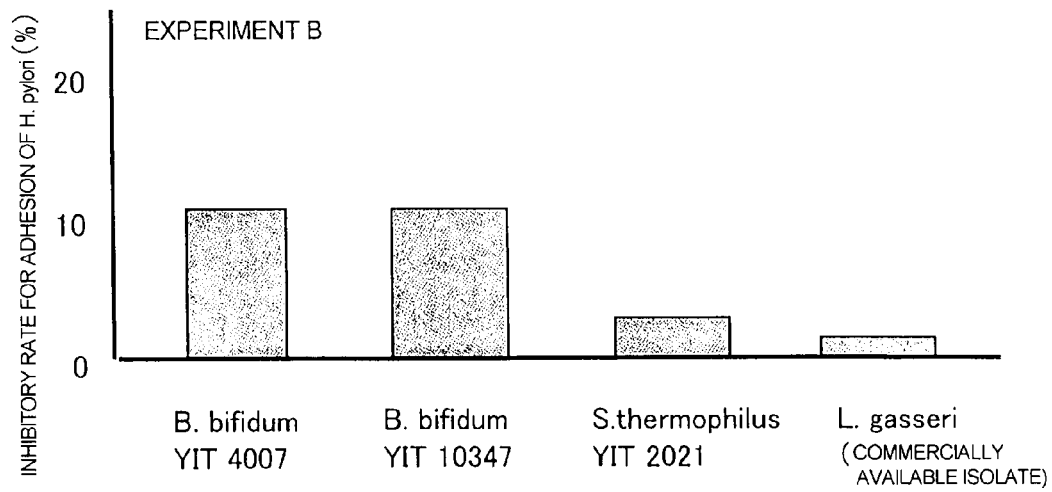
[Fig.7]
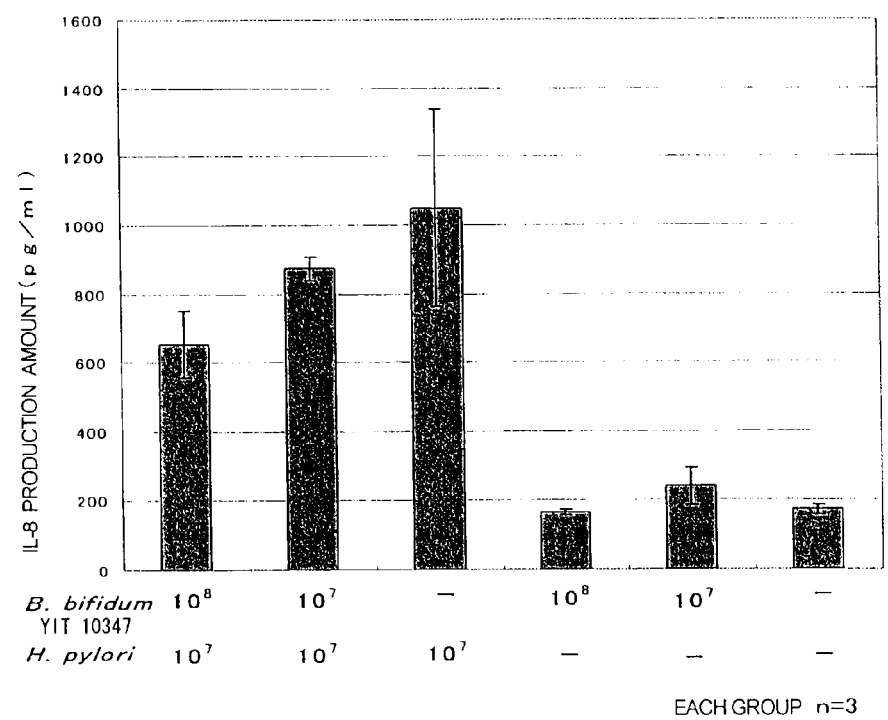

[Fig.8]
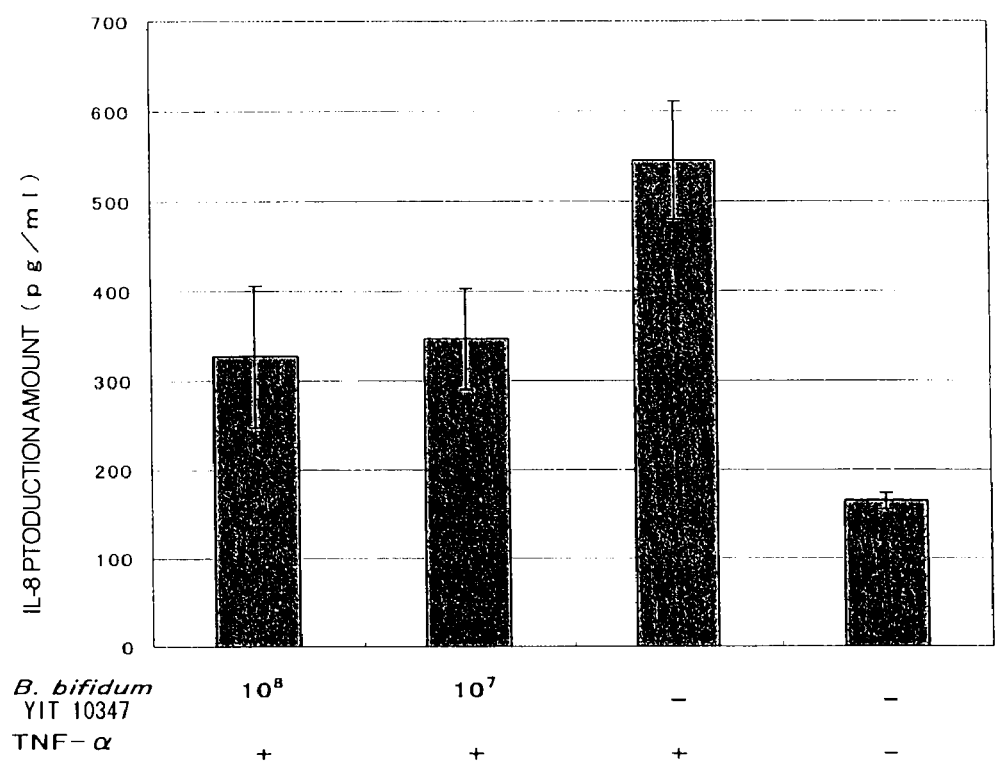

[Fig.9]
EXPERIMENT A
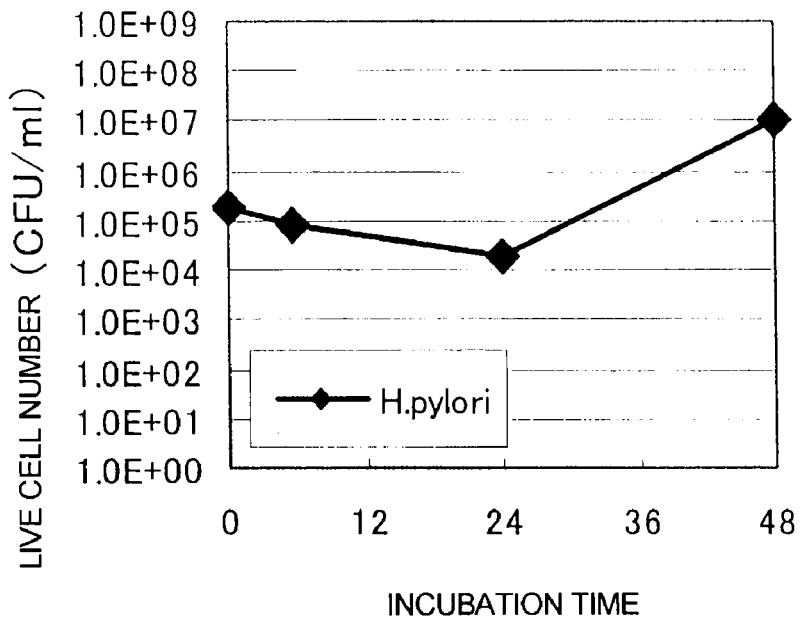
EXPERIMENT B
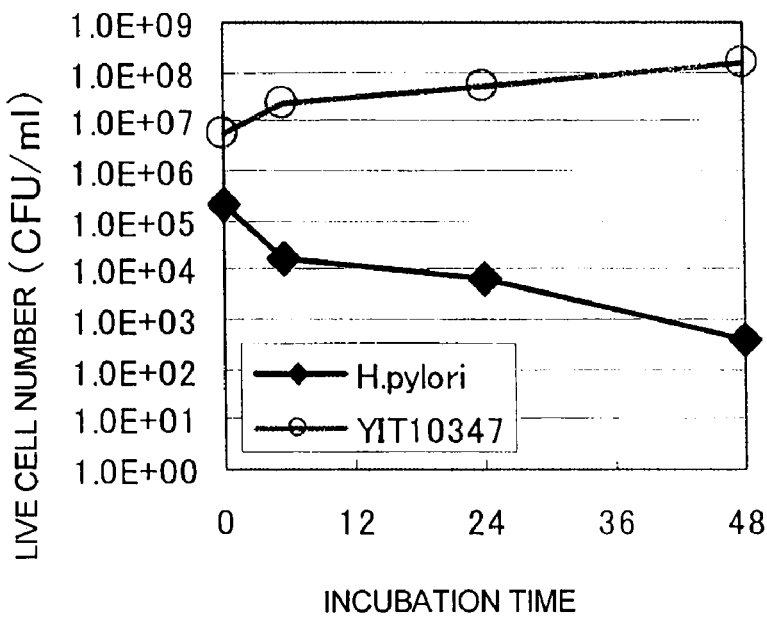

[Fig.10]
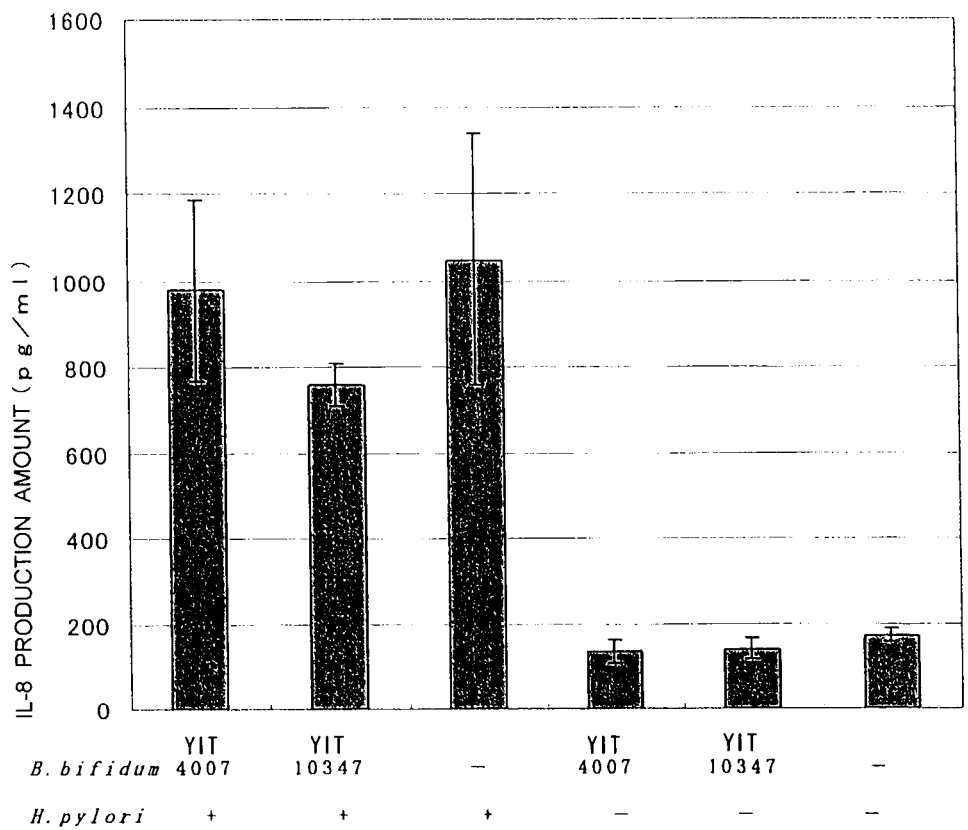
[Fig.11]
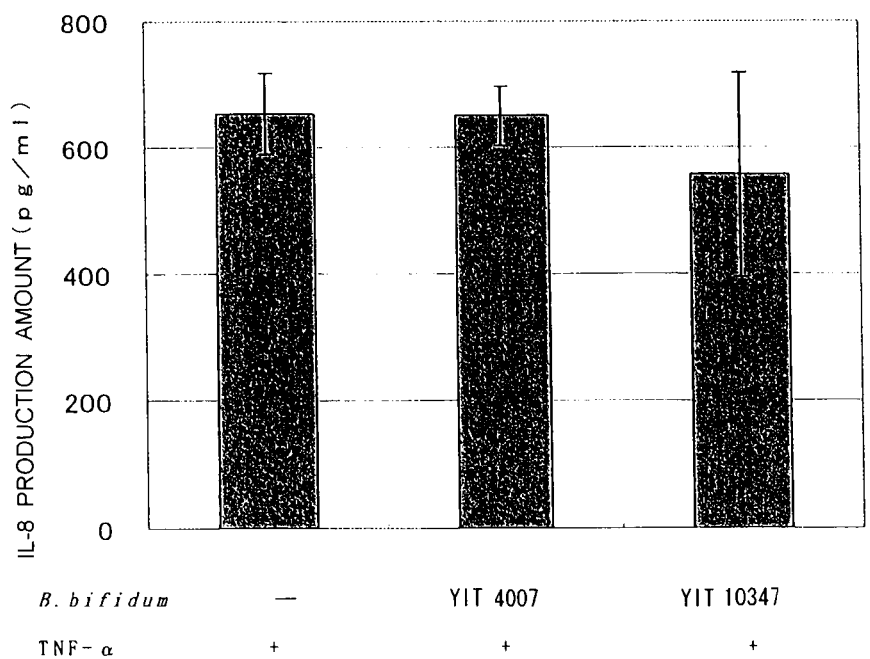

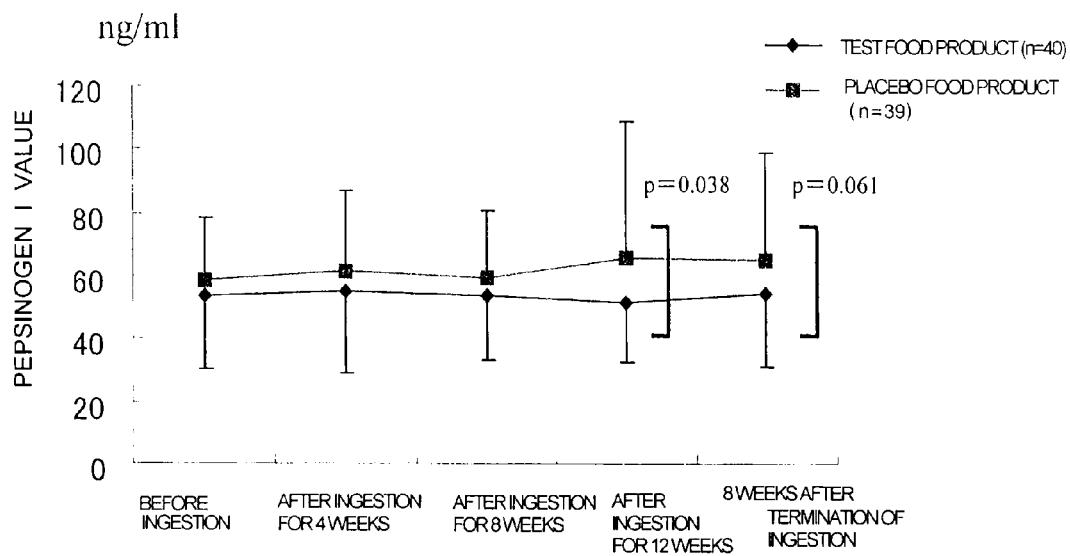
[Fig.12]
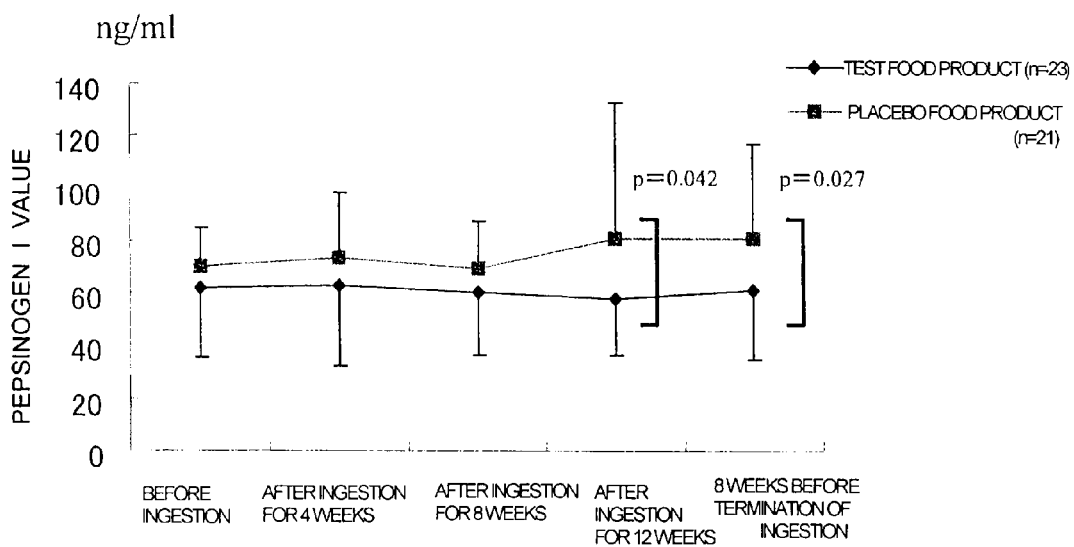
[Fig.13]

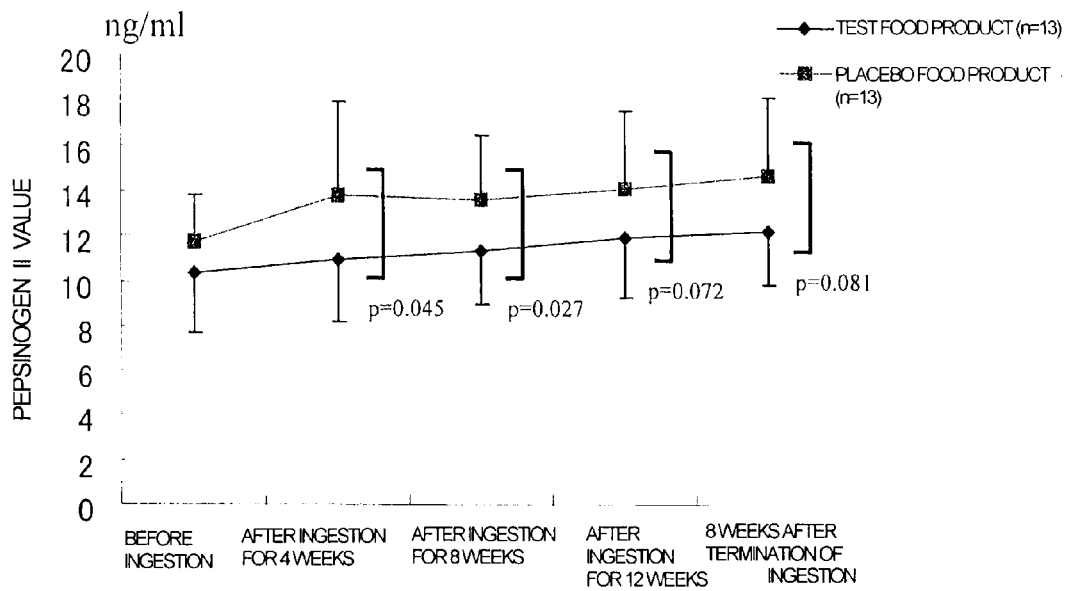
[Fig.14]
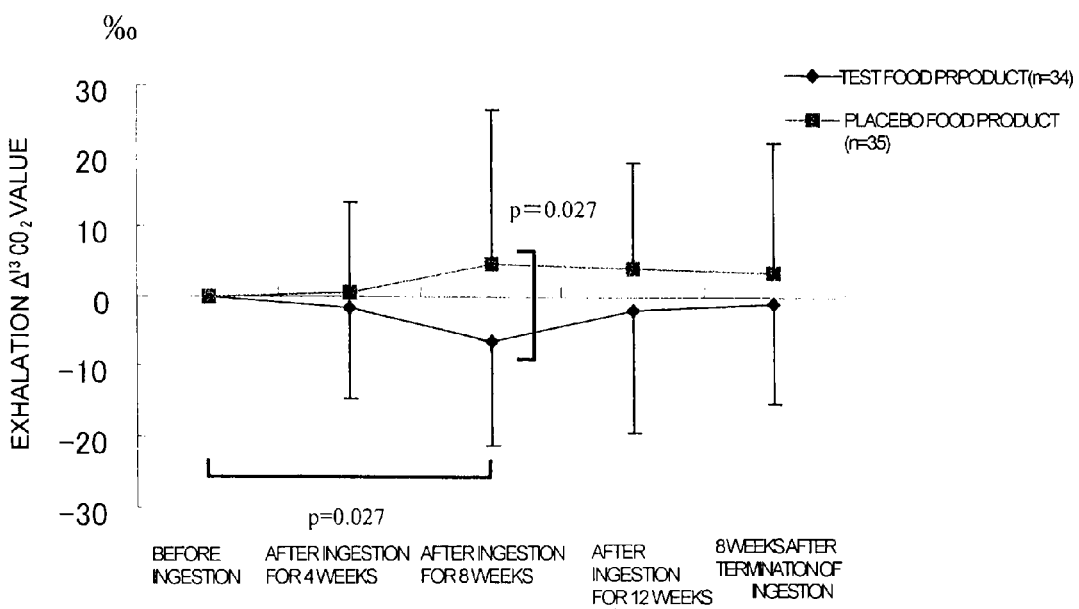
[Fig.15]

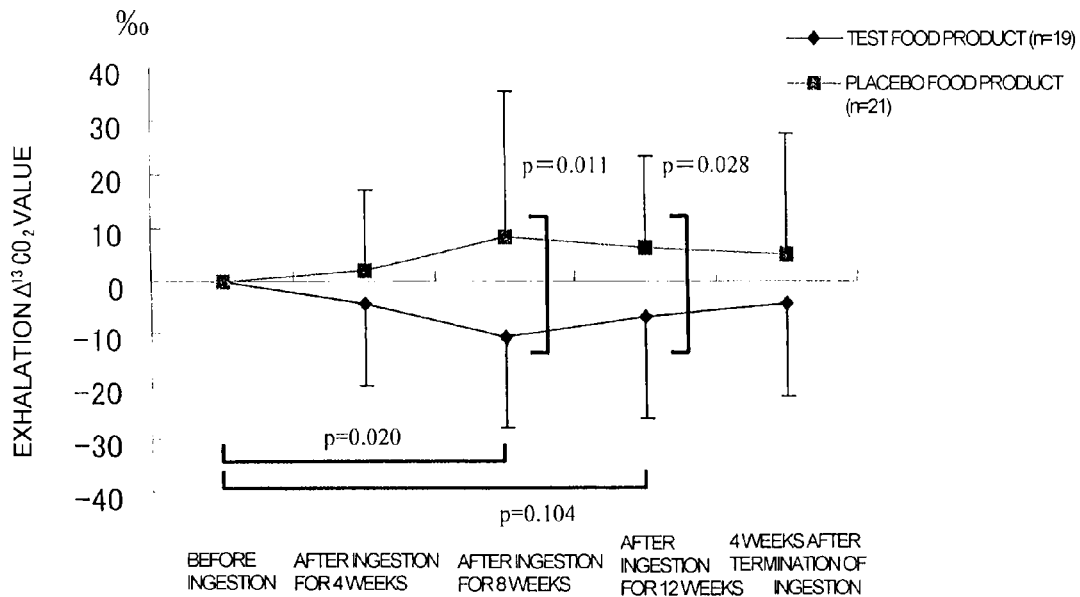
[Fig. 16]
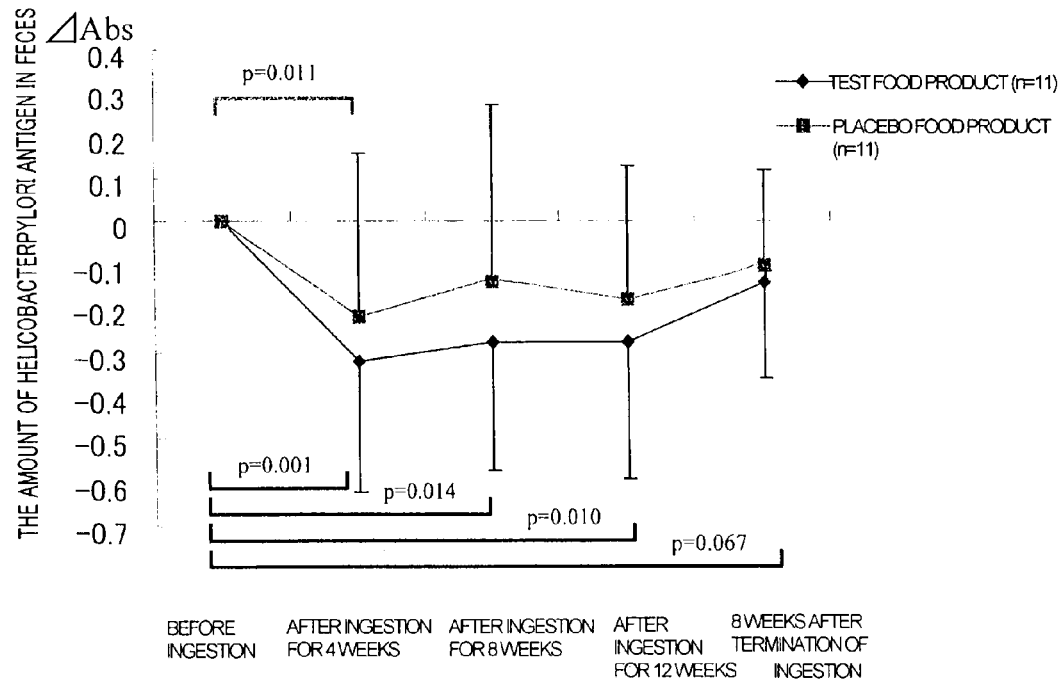
[Fig. 17]

[Fig.18]
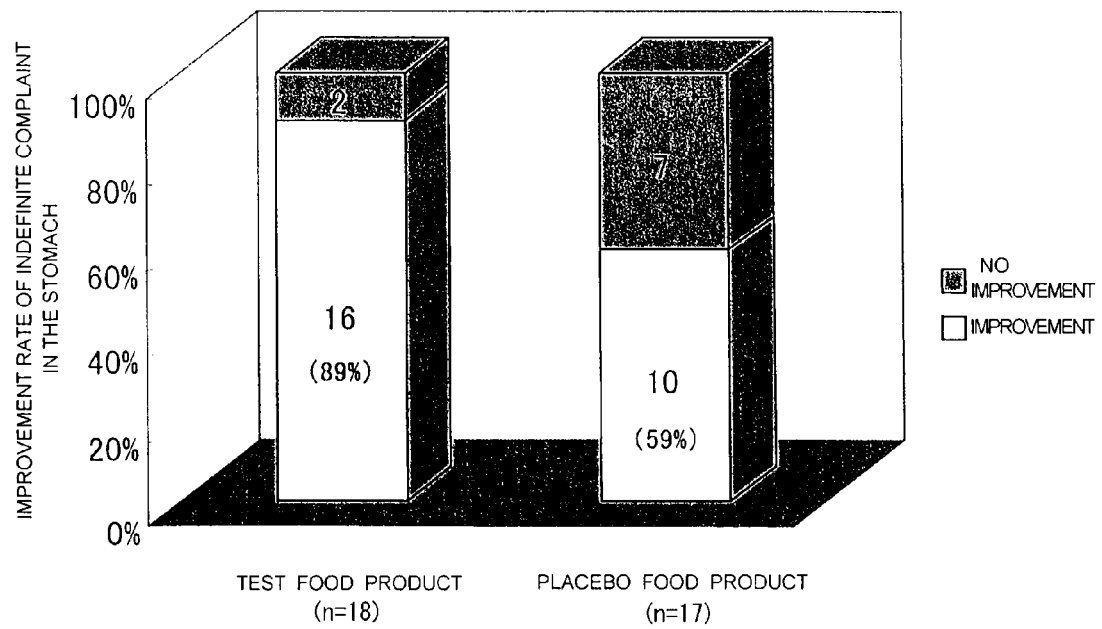

_(1)_

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 1
ccacatgatc gcatgtgatt g                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccgaaggctt gctcccaaa                                                 19

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgcagccaa                                                           10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacgcgcaac                                                           10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggaaatag                                                           10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaggacaaag                                                           10

<210> SEQ ID NO 7
<211> LENGTH: 10
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 7
cgaactagac                                                          10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagacaagc                                                          10
```

BACTERIUM BELONGING TO THE GENUS *BIFIDOBACTERIUM* AND UTILIZATION OF THE SAME

CROSS-REFERENCE TO RELATED APPLICATIONS

The present application is a 35 U.S.C. §371 National Stage patent application of International patent application PCT/JP2006/314369, filed on Jul. 20, 2006, which claims priority to Japanese patent application JP 2005-211670, filed on Jul. 21, 2005.

TECHNICAL FIELD

The present invention relates to a novel *Bifidobacterium bifidum* which has an effect of killing *Helicobacter pylori* and shows high survivability in a fermented milk drink or food, and to the utilization of the same.

BACKGROUND ART

Bacteria belonging to the genus *Bifidobacterium* (hereinafter, referred to as "bifidus bacteria") are major bacteria in the human intestinal bacterial flora, and are known to have favorable effects for human health, such as regulation of the intestinal function including improvement in constipation or diarrhea symptoms, suppression of increase of the serum cholesterol, immune activating effect, and the like. Many commercial products of Bifidus bacteria are available in forms of various fermented milk drinks and foods or live bacterial preparations, establishing a firm market. In particular, the fermented milk drinks and foods containing bifidus bacteria have favorable taste and are fit for continuous ingestion of bifidus bacteria.

With recent progress on the study of the effectiveness of bifidus bacteria, it was found that the bifidus bacteria have an anti-ulcer effect; for example, it has been reported that 3 species of *Bifidobacterium* breve YIT 4014, *Bifidobacterium* breve YIT 4043 and *Bifidobacterium bifidum* YIT 4007 (FERM BP-791) show an anti-ulcer effect in a rat model with ulcer induced by acetic acid (non-patent document 1). In addition, it has been reported that by administering *Bifidobacterium bifidum* YIT 4007 in dried powder form, the condition of patients suffering from gastric ulcer or duodenum ulcer is improved and *Helicobacter pylori* disappear from the gastric mucosa (non-patent document 2). Thus, utilization of the bifidus bacteria has been expected as a preventive or therapeutic agent for infection with *Helicobacter pylori* or as a preventive or therapeutic agent for gastritis, gastric ulcer and duodenum ulcer. Further, it has been reported that the effect of the above-mentioned *Bifidobacterium bifidum* YIT 4007 increases in accordance with the increase in the viable cell count to be administered (non-patent document 3). In order to make effective use of the pharmacological action of *Bifidobacterium bifidum* YIT 4007, it is necessary to allow as many live cells as possible to reach the stomach and intestinal tract.

The bifidus bacteria including *Bifidobacterium bifidum* YIT 4007 are sensitive to oxygen since they are obligatory an aerobes; particularly, when preserved under aerobic condition, a problem arises that they are rapidly reduced in the viable cell count; therefore, it was difficult to administer the sufficient number of bifidus bacteria.

In order to solve this problem, an attempt is being made to make use of various components for improving the survivability in preservation, such as, vegetable juice of pumpkin, cucumber, etc., pyruvic acid, reduced-type glutathione (patent document 1), glycerol, xylitol, etc. (patent document 2), lactitol (patent document 3), and the like. The addition of these components, however, involves problems such as increase in the production cost, decrease in taste, and the like and thus cannot be readily applied. Another attempt is being made to place a fermented product containing a bifidus bacterium in a vessel composed of oxygen-impermeable wrapping material to completely block contact with oxygen. However, such vessel with perfect oxygen-impermeability has not yet been provided, and further there is a problem that materials having low oxygen-permeability are poor in molding flexibility. Moreover, when a composite material is used for a vessel composed of low oxygen-permeable material, problems arise such as treatment of its waste is complicated, the vessel is per se expensive and the like, and thus there is much limitation in its utilization.

It is considered, accordingly, that an ultimate solution for improving the survivability of the bifidus bacteria in fermented milk drinks and foods etc., is to create a strain of bifidus bacteria having high survivability even in aerobic condition; as examples of such bacterial strains, *Bifidobacterium* breve YIT 10001 (FERM BP-8205)(patent document 4), *Bifidobacterium* breve SBR3212 (FERM P-11915) (patent document 5), *Bifidobacterium bifidum* YIT 4002 (FERM BP-1038) (patent document 6), and the like are already been reported.

These bifidus bacteria having high survivability in aerobic condition, however, exhibited much lower activity of killing *Helicobacter pylori* and antiulcer activity compared to *Bifidobacterium bifidum* YIT 4007. Such strain which has high survivability even in aerobic condition and exhibits an activity of killing *Helicobacter pylori* has not yet been created, and it has been difficult to deliver the sufficient number of live cells for expressing an anti-ulcer effect into the stomach or intestinal tract.

Patent document 1: JP-A-2003-250528
Patent document 2: JP-A-11-137172
Patent document 3: Japanese Patent No. 3261571
Patent document 4: WO 03/040350 International Published Pamphlet
Patent document 5: Japanese Patent No. 2922013
Patent document 6: JP-B-61-19220
Non-Patent document 1: The Japanese Society of Carbohydrate Research, 16th Carbohydrate Symposium, Pamphlet, 24-25 (1994)
Non-Patent document 2: Jpn Pharmacol Ther Vol. 22, No. 11, 253-256 (1994)
Non-Patent document 3: Functional Foods and Pharmacological Nutrients Vol. 2, No. 3, 203-213 (2005)

DISCLOSURE OF INVENTION

Problem to be Solved by the Invention

The purpose of the invention, accordingly, is to provide a novel strain of *Bifidobacterium bifidum* which has an effect of killing *Helicobacter pylori* and shows high survivability even in the case of being present in a fermented milk food or drink stored under aerobic condition.

Means For Solving The Problems

The present inventors worked assiduously to solve the above problems and found that *Bifidobacterium bifidum* which had an effect of killing *Helicobacter pylori* and showed high survivability even in the case of being stored under aerobic condition could be obtained by culturing and modifying *Bifidobacterium bifidum* which has an effect of killing *Helicobacter pylori* on the specific conditions. Thus, the invention was completed.

That is, the invention provides *Bifidobacterium bifidum* having the following properties.

(1) Having an effect of killing *Helicobacter pylori*.

(2) Showing a survival rate of 10% or higher in the case of being present in a fermented milk drink or food and stored under aerobic condition at 10° C. for 14 days.

The invention also provides a preventive or therapeutic agent for infection with *Helicobacter pylori*, a preventive or therapeutic agent for gastritis and ulcer, a preventive or therapeutic agent for indefinite complaint in stomach, or a preventive or therapeutic agent for hyperchylia and gastroesophageal reflux, which comprises the above-mentioned *Bifidobacterium bifidum* as an active ingredient.

In addition, the invention provides a drink or food, particularly a fermented milk drink or food, which comprises the above-mentioned *Bifidobacterium bifidum*.

Effect of The Invention

Since *Bifidobacterium bifidum* of the invention is excellent in a survival rate even in the case of being present in a fermented milk drink or food stored under aerobic condition, its effect of killing *Helicobacter pylori* can be maintained over a long period.

Thus, *Bifidobacterium bifidum* of the invention can be utilized preferably in prevention or treatment of infection with *Helicobacter pylori*, prevention or treatment of gastritis and ulcer, prevention or treatment of indefinite complaint in stomach, or prevention or treatment of hyperchylia and gastroesophageal reflux. Further, *Bifidobacterium bifidum* of the invention can preferably be utilized in production of drinks and foods having the above-mentioned preventive or therapeutic effect, particularly fermented milk drink and food, and is not necessary to be put in a vessel made of an oxygen-impermeable wrapping material; thus, options of the vessels are broad.

BEST MODE FOR CARRYING OUT THE INVENTION

*Bifidobacterium bifidum* of the invention has an effect of killing *Helicobacter pylori* and shows a survival rate of 10% or higher in the case of being present in a fermented milk drink or food and stored under aerobic condition at 10° C. for 14 days. The term "effect of killing *Helicobacter pylori*" indicates that the cell number of *Helicobacter pylori* decreases due to an inhibitory action for adhesion of *Helicobacter pylori* to the human gastric cell or a direct inhibitory action for the growth of *Helicobacter pylori*. As described herein, the inhibitory action for adhesion of *Helicobacter pylori* to the human gastric cell specifically means that when *Bifidobacterium bifidum* of the invention is added to the cells derived from the human stomach on a Leibovitz's L-15 medium at a rate of $10^8$-$10^9$ CFU/mL and pre-incubated at 37° C. for 2 hours, and *Helicobacter pylori* is added there at $10^7$ CFU/mL and incubated at 37° C. for 90 minutes and allowed to stand at 4° C. overnight, then the adhesion of *Helicobacter pylori* to the human gastric cell is inhibited by 5% or more, preferably by 5-20%. Alternatively, it may mean that when $10^7$ CFU/mL of *Helicobacter pylori* and $10^8$-$10^9$ CFU/mL of *Bifidobacterium bifidum* of the invention are pre-incubated on a Leibovitz's L-15 medium at 37° C. for 2 hours, and the pre-incubated solution is added to the cells derived from the human stomach and incubated at 37° C. for 90 minutes and allowed to stand at 4° C. overnight, then the adhesion of *Helicobacter pylori* to the human gastric cell is inhibited by 5% or more, preferably by 5-20%. The inhibitory action for the growth of *Helicobacter pylori* specifically means that when $10^5$ CFU/mL of *Helicobacter pylori* and $10^7$ CFU/mL of *Bifidobacterium bifidum* of the invention are added to a Brucella medium and incubated at 37° C. for 48 hours, the live cell number of *Helicobacter pylori* is reduced to $10^3$ CFU/mL or less, preferably 10-$10^3$ CFU/mL. Decrease of the cell number of *Helicobacter pylori* specifically refers to the reduced number of the cells of *Helicobacter pylori* adhering to gastric cell, gastric mucin or gastric tissue, the reduced number of the cells of *Helicobacter pylori* existing in the intestinal tract such as oral cavity, nasal cavity, throat, esophagus, stomach, duodenum, small intestine, appendix, large intestine, rectum, and the like, the reduced number of the cells of *Helicobacter pylori* in concurrent incubation (mixed culture) with *Helicobacter pylori*, decrease of the $\Delta^{13}CO_2$ value in an urea breath test, decrease of the antibody titer for *Helicobacter pylori* in serum, and decrease of the antigen amount for *Helicobacter pylori* in feces. In this connection, the cell number of *Helicobacter pylori* includes the live cell number (CFU) of *Helicobacter pylori*, the amount of cell (reactivity with an anti-*Helicobacter pylori* antibody), the amount of gene (the amount of DNA or RNA capable of recognizing specifically *Helicobacter pylori*), the amount or activity of an pathogenic factor specific to *Helicobacter pylori* (urease activity, vacuolation toxin VacA, CagPAI (pathogenecity island), the amount of LPS-Lewis antigen). Further, the survival rate refers to the ratio of the viable cell count of a culture broth or a fermented milk drink or food after storage under aerobic condition (10° C., 14 days) to the viable cell count before storage under aerobic condition. The viable cell count can be obtained according to a conventional method. For example, a culture broth or a fermented milk drink or food described later which has been used in storage under aerobic condition is diluted properly, and then smeared on or mixed in a TOS propionic acid agar medium, then incubated at 37° C. anaerobically for 72 hours, and the colony is counted to obtain the number of cells.

Specifically, the *Bifidobacterium bifidum* of the invention can be derived by culturing and modifying *Bifidobacterium bifidum* as a parent strain which has an effect of killing *Helicobacter pylori*. As for *Bifidobacterium bifidum* utilizable as a parent strain, there is no particular limitation as far as it has an effect of killing *Helicobacter pylori*; for example, *Bifidobacterium bifidum* YIT 4007 (it was deposited as FERM BP-791 on Feb. 2, 1981 at International Patent Organism Depository, National Institute of Advanced Industrial Science and Technology (Tsukuba Central 6, 1-1, Higashi 1-chome, Tsukuba-shi, Ibaraki-ken)) may be given.

There is no particular limitation in a method of culturing and modifying; for example, condensation method, a method of mutation by mutagen such as ultraviolet ray, nitrosoguanidine (NTG), ethylmethanesulfonic acid (EMS), and the like are given.

A specific example of breeding and modifying will be explained by a condensation method. *Bifidobacterium bifidum* as a parent strain which has an effect of killing *Helicobacter pylori* is first incubated on a milk medium to give a culture broth, which is stored under aerobic condition. Among those organism that survived, a high oxygen resistant strain is selected from the survived organisms. More specifically, *Bifidobacterium bifidum* YIT4007 (FERM BP-791) is incubated on a milk medium to give a culture broth, to which is then added a syrup solution to prepare a fermented milk drink or food; and then the fermented milk drink or food is stored under aerobic condition for 21 days, and the survived organisms are selected. Using the organisms selected as mentioned above, the same process is repeated so that the organisms having a high oxygen resistance is concentrated. Thus, the *Bifidobacterium bifidum* of the invention showing a survival rate of 10% or higher, preferably 10 to 40%, in the case of being present in a fermented milk drink or food under aerobic condition at 10° C. for 14 days can be obtained. An example of storage under aerobic condition includes storage under aeration and agitation in which atmosphere is passed through a storage system by continuous stirring with a stirring bar or stirring blade in aerobic state.

The milk culture medium used in the above condensation method refers to a culture medium containing milk as a major ingredient, wherein the milk includes cow's milk and processed product thereof, such as skim milk, and peptides derived from milk. There is no particular limitation in the culture condition for incubating *Bifidobacterium bifidum* in a milk culture medium, which may be set as appropriate in accordance with the growth condition of *Bifidobacterium bifidum*; in general, it is appropriate to conduct the culture anaerobically at 30-40° C., preferably 33-37° C. Among *Bifidobacterium bifidum*, there is a strain which is difficult to grow on because its sole nutritional source is milk; in such case, a growth accelerating substance such as various sugars, yeast extract, peptides, and the like may be added.

In storing the culture broth by the above condensation method in aerobic condition, optional ingredients such as sweetener, e.g., syrup, emulsifying agent, thickener (stabilizer), vitamins, minerals, acidifier, milk fat, flavor, extract, and the like may be added. If required, other microorganisms than *Bifidobacterium bifidum* may be used in combination in a known method to obtain a form of fermented milk drinks or foods for condensation. In such a case, the environment is very near the final form of the product in comparison to the case in which a culture broth alone is used; thus, the bacterium which shows high survivability in the final form of product can be concentrated more efficiently.

Among the optional ingredients added to the culture broth, the syrup includes sugars such as glucose, sucrose, fructose, isoglucose, paratinose, trehalose, lactose, xylose, malt sugar, honey, molasses, and the like, sugar alcohol such as sorbitol, xylitol, erythritol, lactitol, paratinit, reduced starch syrup, reduced malt sugar syrup, and the like, highly-sweet sweetener such as aspartame, thaumatin, sucralose, acesulfame-K, stevia, and the like. The emulsifying agent includes sucrose fatty acid esters, glycerin fatty acids esters, polyglycerin fatty acid esters, sorbitan fatty acid esters, lecithin, and the like. The thickener (stabilizer) includes agar, gelatin, carrageenan, guar gum, xanthan gum, pectin, locust bean gum, gellan gum, carboxymethylcellulose, soybean polysaccharides, alginic acid propylene glycol, and the like. The vitamin includes vitamin A, vitamins B, vitamin C, vitamins E, and the like. The mineral includes calcium, magnesium, zinc, iron, manganese, and the like. The acidifier includes citric acid, lactic acid, acetic acid, malic acid, tartaric acid, gluconic acid, and the like. The milk fat include cream, butter, sour cream, and the like. The flavor includes yoghurt-type, berry-type, orange-type, chinese quince-type, perilla-type, citrus-type, apple-type, mint-type, grape-type, apricot-type, pear, custard cream, peach, melon, banana, tropical, herb-type, tea, coffee, and the like. The extract includes herb extract, brown sugar lump, and the like.

The microorganism other than *Bifidobacterium bifidum* includes, for example, bacteria belonging to the genus *Bifidobacterium* such as *Bifidobacterium breve, Bifidobacterium longum, Bifidobacterium infantis, Bifidobacterium adolescentis, Bifidobacterium catenulatum, Bifidobacterium pseudocatenulatum, Bifidobacterium animalis, Bifidobacterium lactis, Bifidobacterium globosum*, and the like; bacteria belonging to the genus *Lactobacillus* such as *Lactobacillus casei, Lactobacillus acidophilus, Lactobacillus plantarum, Lactobacillus buchneri, Lactobacillus gallinarum, Lactobacillus amylovorus, Lactobacillus brevis, Lactobacillus rhamnosus, Lactobacillus kefir, Lactobacillus paracasei, Lactobacillus crispatus, Lactobacillus zeae, Lactobacillus helveticus, Lactobacillus salivalius, Lactobacillus gasseri, Lactobacillus fermentum, Lactobacillus reuteri, Lactobacillus crispatus, Lactobacillus delbrueckii* subsp. *bulgaricus, Lactobacillus delbrueckii* subsp. *delbrueckii, Lactobacillus johnsonii, Lactobacillus pentosus, Lactobacillus mali*, and the like; bacteria of the genus *Streptococcus* such as *Streptococcus thermophilus*; bacteria of the genus *Lactococcus* such as *Lactococcus lactis* subsp. *lactis, Lactococcus lactis* subsp. *cremoris*, and the like; bacteria of the genus *Enterococcus* such as *Enterococcus faecalis, Enterococcus faecium*, and the like; bacteria of the genus *Bacillus* such as *Bacillus subtilis*; and yeast belonging to the genera *Saccharomyses, Torulaspora* and *Candida* such as *Saccharomyses cerevisiae, Torulaspora delbrueckii, Candida kefyr*, and the like.

One of the strains obtained by the above condensation method, of which the survival rate was recognized particularly high, was deposited as of Jun. 23, 2005 as *Bifidobacterium bifidum* YIT 10347 (FERM BP-10613) internationally at International Patent Organism Depository, National Institute of Advanced Industrial Science and Technology (Tsukuba Central 6, 1-1, Higashi 1-chome, Tsukuba-shi, Ibaraki-ken)(FERM BP-10613 was turn from FERM P-20569 deposited at the above Depository Authority on Jun. 23, 2005).

The bacteriological properties of *Bifidobacterium bifidum* YIT 10347 (hereinafter, sometimes referred to as "YIT 10347") are shown as follows in comparison with the parent strain *Bifidobacterium bifidum* YIT 4007 (hereinafter, sometimes referred to as "YIT 4007").

<Character of Colony and Morphology>

Each strain was inoculated on an agar MILS medium (Iwata & Morishita, Letter in Applied Microbiology, vol. 9, 165-168, 1989) and incubated at 37° C. anaerobically, and isolation of a single colony was repeated. Thus, the character of the colony of purified strain and the morphological form were observed.

TABLE 1

|  | YIT 4007 | YIT 10347 |
| --- | --- | --- |
| Gram staining | positive | positive |
| Morphological form | polymorphic *bacillus* | polymorphic *bacillus* |
| Colony color | white | white |
| Colony form | smooth planar | smooth planar |

<Results of the Character Test of Sugar Fermentation by API 50CH>

Using API 50CH (product of bioMerieux Japan), a solution of the bacterium after incubation overnight was inoculated to each substrate according to the method as described in the manual attached to the kit. This was incubated at 37° C. in an anaerobic glove box, and the character of sugar fermentation on each substrate was determined on the 7th day after incubation.

TABLE 2

| | YIT 4007 | YIT 10347 |
|---|---|---|
| Control | − | − |
| Glycerol | − | − |
| Erythritol | − | − |
| D-Arabinose | − | − |
| L-Arabinose | − | − |
| Ribose | − | − |
| D-Xylose | − | − |
| L-Xylose | − | − |
| Adonitol | − | − |
| β Methyl-xyloside | − | − |
| Galactose | + | + |
| D-Glucose | + | + |
| D-Fructose | + | + |
| D-Mannose | − | − |
| L-Sorbose | − | − |
| Rhamnose | − | − |
| Dulcitol | − | − |
| Inositol | − | − |
| Mannitol | − | − |
| α Methyl-D-mannose | − | − |
| α Methyl-D-glucose | − | − |
| N Acetylglucosamine | ± | + |
| Amygdaline | − | − |
| Arbutine | − | − |
| Esculin | − | − |
| Salicin | − | − |
| Cellobiose | − | − |
| Maltose | − | − |
| Lactose | ± | + |
| Melibiose | ± | ± |
| Saccharose | − | + |
| Treharose | − | − |
| Inulin | − | − |
| Melezitose | − | − |
| D-Raffinose | − | − |
| Amidon | − | − |
| Glycogen | − | − |
| Xylitol | − | − |
| β Gentiobiose | ± | + |
| D-Turanose | − | − |
| L-Lyxose | − | − |
| D-Tagatose | − | − |
| D-Fucose | − | − |
| L-Fucose | − | − |
| D-Arabitol | − | − |
| L-Arabitol | − | − |
| Gluconate | − | − |
| 2 Ceto-gluconate | − | − |
| 5 Ceto-gluconate | − | − |

+: positive;
±: psudo-positive;
−: negative

*Bifidobacterium bifidum* of the invention has an effect of killing *Helicobacter pylori*, particularly, inhibitory effect for adhesion of *Helicobacter pylori* to the human gastric cells, and inhibitory effect for the growth of *Helicobacter pylori*. Further, *Bifidobacterium bifidum* of the invention has a protective effect for the gastric mucosa, an effect of improving the serum pepsinogen (PG) value, and an effect of inhibiting the production of interleukin (IL)-8, similar in the parent strain *Bifidobacterium bifidum* YIT 4007 as one example.

Further, in fermented milk drinks and foods produced by using *Bifidobacterium* bacteria or lactic acid bacteria, some changes with time such as increase of acidity are observed during storage, deteriorating the taste. It is known that this deterioration with age increases when disaccharides such as sucrose is used, and particularly, this is remarkable in a higher concentration of milk solid non fat (SNF). Using *Bifidobacterium bifidum* of the invention, however, the increase of acidity is suppressed during storage even in the case of using disaccharide such as sucrose in the fermented milk drinks or foods, though its mechanism is not understood; thus, deterioration of a taste can be suppressed. In a specific case, when the *Bifidobacterium bifidum* of the invention is used in a fermented milk drink or food containing 3 mass % or more, preferably 3-6 mass % of sucrose, and 8 mass % or more, preferably 8-12 mass % of fat-free milk solid portion, and stored at 20° C. for 4 days in aerobic condition, the difference of the acidity before (immediately after production) and after storage is 2 or less, preferably 1 or less. In this situation, the acidity means the amount of 1/10 normal sodium hydroxide aqueous solution (mL) required for neutralizing 9 g of a sample.

*Bifidobacterium bifidum* of the invention having the above-mentioned properties, since it has an effect of killing *Helicobacter pylori*, can be utilized as a preventive or therapeutic agent for infection with *Helicobacter pylori*. The killing effect as a pharmacological action of the *Bifidobacterium bifidum* of the invention is increased with increase of the viable cell count, and therefore, it is desirable to use *Bifidobacterium bifidum* of the invention in a state of live organisms. Further, since *Bifidobacterium bifidum* of the invention has a high oxygen resistance, a large number of live cells can be sent to the stomach and intestinal tract, it can be used suitably in prevention or therapy of infection with *Helicobacter pylori*, in prevention or therapy of gastritis and ulcer, in prevention or therapy of indefinite complaint in stomach, or in prevention or therapy of hyperchylia and gastroesophageal reflux.

*Bifidobacterium bifidum* of the invention, since it has a preventive effect for the gastric mucosa and an effect of improving the serum pepsinogen (PG) value, can be utilized in treatment or improvement or prevention of stress ulcer, necrotic ulcer caused by alcohol, etc., active gastritis, vestibular dominant gastritis, gastritis dominant in the body of stomach, pangastritis, gastric adenoma, hyperplastic polyp, polyp in fundic glands, atrophic gastritis, gastroesophageal reflux (reflux esophatitis), indefinite complaint in stomach (including Non-ulcer dyspecpia) and stomach cancer closely relating to infection with *Helicobacter pylori*.

In the gastric mucosa infected with *Helicobacter pylori*, active gastritis (cortex gastritis), which is a histological gastritis characterized by infiltration of neutrophile and a large amount of mononuclear cells, is caused. With progress of the gastritis, the growth of the cells is suppressed, the cell function degrades, and the mucosa weakens, resulting in atrophic gastritis in which no active inflammatory image is observed. With progress of the atrophic gastritis, intestinal epitherial metaplasia is caused to increase the risk of stomach cancer. On the other hand, tissue breakdown of the gastric mucosa which is caused by an influence of a challenge factor such as gastric acid or pepsin or drugs such as NSAIDs in a state of active gastritis results in peptic ulcer such as gastric ulcer or duodenum ulcer. Therefore, *Bifidobacterium bifidum* of the invention having an effect of killing *Helicobacter pylori* can be utilized as a preventive or therapeutic agent for gastritis or ulcer caused by *Helicobacter pylori*, particularly for gastric and duodenum ulcers. Further, *Bifidobacterium bifidum* of the invention, since it decreases the serum pepsinogen I value which strongly correlates with secretion of gastric acid, can be utilized as a preventive or therapeutic agent for hyperchylia or as a preventive or therapeutic agent for gastroesophageal reflux (reflux esophatitis) occurring after treatment with killing of *Helicobacter pylori* with an antibiotic.

Infection with *Helicobacter pylori* induces an inflammatory cytokine such as IL-8, IL-1β, or TNF-α. IL-8 works to migrate neutrophile to the gastric mucosa and cause an inflammatory reaction locally. IL-1β and TNF-α act to induce the production of IL-8, and further decrease secretion of gastric acid, and they are said to have relation to atrophy of the gastric mucosa; thus, the infection with *Helicobacter pylori* which has a high cytokine inducibility causes the gastric mucosa chronic inflammatory state to cause damage to the function of gastric mucosa. *Bifidobacterium bifidum* of the invention is able to suppress the production of IL-8 induced by infection with *Helicobacter pylori* or TNF-α. In addition, the inhibitory effect is higher than that of *Bifidobacterium bifidum* YIT 4007 as an example of parent strains, and increases in accordance with increase of the viable cell count.

When *Bifidobacterium bifidum* of the invention is used as a preventive or therapeutic agent for infection with *Helicobacter pylori*, a preventive or therapeutic agent for gastritis and ulcer, a preventive or therapeutic agent for indefinite complaint in stomach, or a preventive or therapeutic agent for hyperchylia and gastroesophageal reflux, there is no particular limitation in the form of *Bifidobacterium bifidum* as an active ingredient as far as it is in a state of live organism, including lyophilizate or a culture product containing the bacterium.

The above-mentioned preventive or therapeutic agent for infection with *Helicobacter pylori*, the preventive or therapeutic agent for gastritis and ulcer, the preventive or therapeutic agent for indefinite complaint in stomach, or the preventive or therapeutic agent for hyperchylia and gastroesophageal reflux may be administered in a form of conventional pharmaceutical preparations prepared by mixing or combining an active ingredient *Bifidobacterium bifidum* with solid or liquid innoxious carriers for pharmaceuticals. Such a preparation includes, for example, solid preparations such as tablets, granules, powders, or capsules, liquid preparations such as solutions, suspensions or emulsions, and lyophilized preparations. These preparations may be prepared by known preparation methods in the pharmaceutical technology. The above-mentioned innoxious carrier for pharmaceuticals includes, for example, glucose, lactose, sucrose, starch, mannitol, dextrin, fatty acid glyceride, polyethylene glycol, hydroxyethyl starch, ethylene glycol, polyoxyethylene sorbitan fatty acid esters, amino acids, gelatin, albumin, water, physiological saline, and the like. If required, a known excipient or excipients such as a stabilizer, moistening agent, emulsifying agent, binder, tonicity adjusting agent, filler, and the like may appropriately be added. The active ingredient *Bifidobacterium bifidum* may be administered as a single preparation or in combination with a gastric acid secretion inhibitor used for peptic ulcer, reflux esophatitis, gastroesophageal reflux or functional dyspepsia, including $H_2$-receptor inhibitor such as cimetidine, ranitidine, famotidine, roxatidine, nizatidine, lafutidine, ranitidine, and the like; proton pump inhibitor such as omeprazole, lansoprazole, rabeprazole, and the like; gastric mucosa protective agent such as ecabet sodium, ornoprostil, enprostil, misoprostol, cetraxate, sucralfate, sofalcone, troxipide, plaunotol, teprenone, polaprezinc, benexate hydrochloride betadex, rebamipide, sulpiride, selectin, irsogladinemaleate, and the like to administer each active ingredient concurrently. As used herein, the gastric mucosa protective agent includes drugs or ingredients having an effect of enhancing protective factor, an effect of enhancing the expression of cyclooxygenase, an effect of enhancing the production of prostaglandins, an effect of enhancing the secretion of mucus, a cytoprotection effect, an effect of increasing the blood flow in mucosa, an effect of suppressing the secretion of gastric acid, an effect of enhancing the secretion of bicarbonate ion, an anti-gastrin effect, an anti-oxidation effect, an effect of enhancing the generation of endogenous selectin and the like. The active ingredient administered concurrently with *Bifidobacterium bifidum* includes anti-muscarine agent such as pirenzepine hydrochloride, atropine sulfate, and the like; an antacid such as sodium hydrogen carbonate, magnesium oxide, aluminum hydroxide gel/magnesium hydroxide combined solution, aluminum silicate, and the like; naturally occurring materials such as ascorbic acid, uric acid, albumin-binding bilirubin, β-carotene, vitamin E, coenzyme Q, glutathione, cysteine, cystine, pyruvic acid, phytin, phytic acid, lignin, saponin, ferulic acid, γ-aminobutyric acid, γ-orizanol, and the like; and polyphenol such as isoflavone, anthocyanin, catechin, flavone, flavonol, flavanone, chalcone, xanthone, proanthocyanin, fruit polyphenol, tea leaf polyphenol, cacao polyphenol, coffee polyphenol, green tea polyphenol, and the like.

*Bifidobacterium bifidum* which is an active ingredient in the preventive or therapeutic agent for infection with *Helicobacter pylori*, the preventive or therapeutic agent for gastritis and ulcer, the preventive or therapeutic agent for indefinite complaint in stomach, or the preventive or therapeutic agent for hyperchylia and gastroesophageal reflux in the invention has already been utilized as food, and its safety has been confirmed. When it is used as preventive or therapeutic agent for infection with *Helicobacter pylori*, the preventive or therapeutic agent for gastritis and ulcer, the preventive or therapeutic agent for indefinite complaint in stomach, or the preventive or therapeutic agent for hyperchylia and gastroesophageal reflux, there is no strict limitation in the dosage, though the preferred dosage is as the viable cell count $10^5$ CFU-$10^{13}$ CFU, particularly $10^9$ CFU-$10^{13}$ CFU a day.

The preventive or therapeutic agent for infection with *Helicobacter pylori*, the preventive or therapeutic agent for gastritis and ulcer, the preventive or therapeutic agent for indefinite complaint in stomach, or the preventive or therapeutic agent for hyperchylia and gastroesophageal reflux in the invention can be used not only as the above-mentioned pharmaceutical preparations but also in combination with drinks or foods. In the case of combining with drinks or foods, it may be added thereto as such or together with a variety of nutritional ingredients. The drinks and foods can be utilized as health foods or food materials useful in prevention or improvement or treatment of infection with *Helicobacter pylori*, or in prevention or improvement or treatment of gastritis, ulcer, indefinite complaint in stomach, hyperchylia or gastroesophageal reflux. Specifically, when the preventive or therapeutic agent for infection with *Helicobacter pylori*, the preventive or therapeutic agent for gastritis and ulcer, the preventive or therapeutic agent for indefinite complaint in stomach, or the preventive or therapeutic agent for hyperchylia and gastroesophageal reflux is used in combination with drinks or foods, proper additives which can be used in drinks and foods may be used for molding into a form suitable for foods by a known method, that is, granules, grains, tablets, capsules, paste, and the like, or alternatively it may be added to a variety of foods, for example, processed meat products such as ham or sausage; seafood processing products such as boiled fish paste or fish sausage; bread, confectionary, butter, dry milk, and the like, or it may be added to drinks such as water, fruit juice, milk, soft drink, tea drink, and the like. *Bifidobacterium bifidum* of the invention, since it has a high oxygen resistance and does not require strict anaerobic condition, can be adapted to every form of drinks and foods. The drinks and foods include feeds for animal use.

To the above-mentioned drinks or foods may be added a variety of raw materials for food products. For example, various sugars such as glucose, sucrose, maltose, fructose, tagatose, lactose, isoglucose, trehalose, trehallose, agarooligosaccharide, nigerooligosaccharide, galactooligosaccharide, fructooligosaccharide, xylooligosaccharide, raffinose, stachyose, lactulose, malttriose, isomaltooligosaccharide, cyclodextrin, honey, maple syrup, brown sugar, and sweet potato syrup; various nutrients such as meat extract, yeast extract, fish meat extract, heart extract, liver extract, and peptides; various food fibers or their various hydrolysates or extracts such as alginic acid, sodium alginate, fucoidan, sargassan, fulceran, funoran, porphyran, laminaran, pullulan, tara gum, konjak mannan, inulin, β-glucan, chitin, chitosan, polydextrose, hyaluronic acid, chondroitin sulfate, heparan sulfate, polysaccharide sulfate, ganglioside, sulfatide, sialic acid, polysialic acid, mannan, galactan, fructan, xylan, arabinan, arabinogalactan, glucomannan, galactomannan, beet fiber, oat meal fiber, wheat fiber, soybean fiber, rice fiber, barleycorn fiber, xanthan gum, corn fiber, apple fiber, citrus fiber, psyllium fiber, pine fiber, prune fiber, banana fiber, acetic acid bacterium cellulose, lactic acid bacterium cell wall, *Bifidobacterium* cell wall, yeast cell wall, fermented soybean fructan, collagen, and fermented soybean polyglutamic acid; and various raw materials containing a large amount of hardly digestible food fiber or extracted ingredient thereof such as wheat bran, barleycorn bran, rice bran, oat bran, oat meal bran, rye bran, psyllium, rice polishing, raw rice, chicory, soybean refuse, apple pulp, resistant starch, barley malt, corn seed hull, lactic acid bacterium cell, *Bifidobacterium* cell, beer yeast cell, wine yeast cell, baker's yeast cell, wine lees, sake lees, soy source lees, beer lees, rice koji, wheat koji, soy koji, red koji, yellow koji, fermented soybean mucosa, grape seed extract, honey, loyal jelly, propolis, *Chlorella*, spirulina, Euglena, Aloe, wakame (a kind of seaweed), egonori, iwanori, ogonori, kawanori, tengusa, kombu, hondawara, arame, kajime, Asakusa layer, green layer, hijiki, sea lettuce, and mozuku; may be added.

In addition, the followings may be added to the above drinks or foods: a variety of minerals or their salts such as calcium, magnesium, zinc, iron, and dolomite; a variety of acids or salts thereof, such as citric acid, malic acid, tartaric acid, gluconic acid, succinic acid, fumaric acid, ascorbic acid, lactic acid, acetic acid, propionic acid, butyric acid, phosphoric acid, and amino acids; a variety of naturally occurring ingredients such as glutathione, phytin, phytic acid, lignin, saponin, ferulic acid, γ-aminobutyric acid, γ-orizanol, chalcone, flavanone, flavone, flavonol, isoflavone, anthocyan, catechin, proanthocyanidine, tea leaf polyphenol, curcumide, capsaicinoid, sesaminol, gomalignan, teaflavine, β-diketones, carotinoids, allyl sulfur compounds, isothiocyanates, terpenes, chlorophylls, saturated fatty acids, n-3 poly unsaturated fatty acids, n-6 poly unsaturated fatty acids, conjugated linoleic acids, phospholipids, plant sterols, egg proteins, milk proteins, rice proteins, barely proteins, wheat proteins, fish meat proteins, and collagen; a variety of vitamins such as vitamin A, vitamins B, vitamin C, vitamins D, vitamin E, vitamins K, β-carotene, retinoic acid, and folic acid; a variety of extracts or their ingredients of black cohosh, pumpkin seeds, pomegranate seeds, St. John's wort, passion flower, valerian, *Pueraria mirifica*, rosemary, peppermint, parsley, marry gold, lemon balm, mugwort, safflower, Japanese radish seeds, coffee tree, *Acanthopanax* sieboldianum, bottle gourd fruit, citrus fruit skin, ginkgo leaf, dokudami (Saururaceae), jujube tree, Gouqizi, Licorice root, Reishi mushroom, *Panax* ginseng, guarana, mactis sap and the like; a variety of plants or extracts thereof such as green tea, black tea, oolong tea, hydrangea tea, *gymnema* tea, and guava leaf; and a variety of spices such as pepper, Japanese pepper, turmeric, cinnamon, mustard, paprika, turmeric, *Salvia officinalis*, thyme, basil, *capsicum*, and nutmeg.

In addition, the followings may be added to the above drinks or foods: a variety of cereals (every part including leaf, stem, seed, root, flower, bud, hull, sap, and fruit) or the components of their germinated seeds or their extracted components such as rice, hulled rice, barley, wheat, oat meal, rye, oat, corn, amaranthaceous plant, German millet, millet, buckwheat, Job's tear, sawa millet, sorghum, grain sorghum, kudzu-vine, and cassaya; a variety of vegetables (every part including leaf, stem, seed, root, flower, bud, hull, sap, and fruit) or their germinated seeds or their extracted components such as pumpkin, cucumber, sponge-gourd, mioga ginger, celery, eggplant, onion, garlic, avocado, Azuki bean, white Azuki bean, common bean, kidney bean, peas, scarlet runner bean, chanamame bean, white soybean, brown soybean, green soybean, young soybean, mung bean, broad bean, daifuku bean, rennzu bean, red lentil, purple sweet potato, Ashitaba, kale, turmeric, dandelion, potato, sweet potato, taro, konjak, yam, eggplant, tomato, quinine melon, bell pepper, sesame, cabbage, waxgourd, broccoli, cauliflower, lettuce, ginger, burdock, aroid, gourd, spear of Japanese angelica-tree, Japanese radish, Japanese horse-radish, chili pepper, carrot, spinach, lily, scallion, *perilla*, white stemmed onion, gynmight, parsnip, Japanese silver leaf, red garlic, Chinese cabbage, parsley, basil, bracken, field horsetail, royal fern, and bamboo shoots; mushrooms or their extracted components such as Shiitake, mushroom, Maitake, winter mushroom, tree ear, Hatakeshimeji, Bunashimeji, Nameko, oyster mushroom, Eringii, and Matsutake; fruits (every part including leaf, stem, seed, root, flower, bud, hull, sap, and fruit) or their extracted components such as grape, persimmon, lemon, apple, cherry, plum, strawberry, orange, guava, banana, blue berry, black berry, cranberry, raspberry, deer berry, Chinese bayberry, *feijoa*, tree tomato, acerola, olive, coconut, lime, seakuwasar, melon, peach, Chinese bayberry, lychee, mango, Yuzu, papaya, pineapple, pear, plum, grapefruit, Chinese quince, apricot, Japanese apricot, Natsumikan, loquat, mandarin, pomegranate, terminalia beberica, water melon, Japanese plum, European plum, and kiwifruit; and a variety of nuts (every part including leaf, stem, seed, root, flower, bud, hull, sap, and fruit) or their extracted components such as almond, cashew nut, peanut, pine nut, *macadamia* nut, chestnut, ginkgo nut, walnut, cacao, and coffee.

In addition, milk proteins or their hydrolyzates such as casein or whey protein, or milk components such as milk peptides, amino acids, whey, butter milk, milk fats, the membrane of milk fat spherule, lactoferrin, or sialic acid-containing oligosaccharide may be added to the above drinks or foods.

In addition, the following food raw materials having an anti-pylori bacterium effect may be added to the above drinks or foods: the product of the Maillard reaction, melanoidin, chicken yolk protein containing an anti-pylori egg antibody, cocoa, chocolate, coffee, green tea, oolong tea, black tea, infusion of perched barley, wine, beer, Shaoxing rice wine, sake, and ethanol.

Among the above drinks or foods, fermented milk, lactic acid bacteria beverage, fermented soy milk, fermented fruit juice, or fermented vegetable liquid, which contains *Bifidobacterium bifidum* in a form of live cells as an active ingredient, is preferred. These fermented milk drinks or foods may be prepared by a known method, for example, *Bifidobacterium bifidum* may be inoculated and incubated alone or concurrently with another microorganism on a sterilized milk medium, and the product is homogenized to yield a fermented milk base. Subsequently, a separately prepared syrup solution is added thereto and homogenized with a homogenizer, to which is further added a flavor or food raw material to yield the final product. Thus resulting fermented milk may be formulated into any type of product including plane type, soft type, fruit flavor type, solid form, and liquid form.

When the fermented milk drinks or foods are prepared by using *Bifidobacterium bifidum* in combination with one or more species of lactic acid bacteria selected from *Lactobacillus* bacteria, *Streptococcus* bacteria and *Lactococcus* bacteria, they have better taste and thus allowing continuous drinking, which is preferable.

Further, in *Bifidobacterium bifidum* of the invention, increase of the acidity during storage is suppressed even in the case of using a sweetener such as disaccharide, particularly sucrose, and deterioration of the taste is suppressed, and accordingly, it can be utilized suitably to fermented milk drinks or foods which contain the above additives.

So far, the drinks or foods containing a bifidus bacterium have been placed principally in vessels composed of an oxygen impermeable wrapping material such as glass or aluminum-coated paper. *Bifidobacterium bifidum* of the invention, however, has a high oxygen resistant property and requires no strict anaerobic condition; so, a drink or food containing this organism may be put in any kind of vessel, of which the wrapping material of the vessel may be either oxygen permeable or oxygen impermeable. Since an oxygen permeable wrapping material is less expensive and has higher flexibility in molding than an oxygen impermeable wrapping material in preparing a vessel, it is preferable to use a vessel composed of an oxygen permeable wrapping material. Such a vessel composed of an oxygen permeable wrapping material includes those in which the amount of permeable oxygen per vessel is 0.05 mL or more/24 h atm at 25° C. (e.g., polystyrene vessel (polystyrene surface area 125.6 cm$^2$, aluminum cap surface area 5 cm$^2$ (the amount of oxygen permeating the aluminum cap portion is 0 mL)): 2.1 mL/24 h atm at 25° C.; low density polyethylene vessel (low density polyethylene surface area 125.6 cm$^2$, aluminum cap surface area 5 cm$^2$ (the amount of oxygen permeating the aluminum cap portion is 0 mL)): 1.4 mL/24 h atm at 25° C.; high density polyethylene vessel (high density polyethylene surface area 125.6 cm$^2$, aluminum cap surface area 5 cm$^2$ (the amount of oxygen permeating the aluminum cap portion is 0 mL)): 0.63 mL/24 h atm at 25° C.; polyethylene terephthalate vessel (polyethylene terephthalate surface area 125.6 cm$^2$, low density polyethylene cap surface area 5 cm$^2$): 0.08 mL/24 h atm at 25° C.; ethylene vinyl alcohol—low density polyethylene compound vessel (ethylene vinyl alcohol surface area 125.6 cm$^2$, low density polyethylene lid surface area 20.9 cm$^2$): 0.23 mL/24 h atm at 25° C.; ethylene vinyl alcohol—high density polyethylene compound vessel (ethylene vinyl alcohol surface area 125.6 cm$^2$, high density polyethylene lid surface area 20.9 cm$^2$): 0.10 mL/24 h atm at 25° C., etc.) (the amount of oxygen permeating is shown per 100 mL volume vessel in all cases).

The invention will be explained in more detail by the following Examples and Test Examples which are not intended as a limitation thereof.

EXAMPLE 1

Breeding and Improvement of *Bifidobacterium bifidum* YIT 4007

*Bifidobacterium bifidum* YIT 4007 (FERM BP-791) as a parent strain was inoculated on skim milk containing 14 mass % fat-free milk solid portion and incubated at 37° C. up to pH 4.8 to give a cell solution. To this cell solution was added a solution of *Streptococcus thermophilus* YIT 2021 which had separately been inoculated and incubated on skim milk containing 14 mass % fat-free milk solid portion at 37° C. up to pH 4.3 (mixing ratio: 20: 1), and finally a syrup containing isoglucose was added thereto so that the final concentration was 3 mass %, yielding a fermented milk drink or food.

This fermented milk drink or food was preserved in aerobic condition as follows, and the organisms having a high oxygen resistant property was selected. The above prepared fermented milk drink or food (10 L) was placed in a 10 L tank, into which air was introduced at a rate of 7 L/min so that the dissolved oxygen concentration was 12 mg/L or higher, and preserved at 2° C. with stirring at 60 rpm. After the lapse of 21 days, the survived cells were collected as parent strains and made a cell solution in the same manner as above, which was further used in preparation of a fermented milk drink or food. This fermented milk drink or food was preserved at 2° C. under aeration and agitation for 21 days. This operation was repeated 3 times to concentrate strains having high survivability; the survived cells from the 3$^{rd}$ concentration procedure were smeared on a TOS propionic acid agar medium (Yakult Pharmaceutical Industry Co., Ltd.) to isolate 24 strains, each as a single colony.

Using one of the above isolated strains and the parent YIT 4007, fermented milk drinks or foods were prepared in the same manner as above. These (100 mL each) were placed respectively in a 100 mL volume vessel composed of an oxygen permeable polystyrene (polystyrene surface area 125.6 cm$^2$; the amount of oxygen permeating (per vessel) 2.1 mL/24 h atm, 25° C.) and stored at 10° C. (under aerobic condition). The cell numbers immediately after preparation and after storage were counted and their survivability was compared. Thus, YIT 10347 was obtained as a microorganism having higher survivability than YIT 4007. As shown in Table 3, the survival rate 14 days after storage was 30% in YIT 10347 in contrast with 2% in YIT 4007.

TABLE 3

| Strain | Cell Number (CFU/mL) | | Survival rate (%) |
| --- | --- | --- | --- |
|  | Immediately after preparation | After 14 days |  |
| YIT 4007 | $1.1 \times 10^9$ | $2.0 \times 10^7$ | 2 |
| TIT 10347 | $2.2 \times 10^9$ | $6.6 \times 10^8$ | 30 |

EXAMPLE 2

Test for the Character of *Bifidobacterium bifidum* YIT 10347

By the following experiments and the comparison of the properties of colonies, the form of the organisms and the properties in sugar fermentation, it was confirmed that *Bifidobacterium bifidum* YIT 10347 is a bred and improved strain of *Bifidobacterium bifidum* YIT 4007 as a parent strain.

(1) Identification of the Species by Species-Specific Primers

DNAs were extracted from 1 mL of the cell solution of *Bifidobacterium bifidum* YIT 10347 and YIT 4007 according to a benzyl chloride method (Nuc. Acid. Res 21, 5279-5280 (1993)) using glass beads. The species of the organisms were confirmed by a PCR method using the primers specific to *Bifidobacterium bifidum* (FEMS Microbiol. Letts. 167, 113-121 (1998)) and the above DNAs as templates. As a result, amplification specific to *Bifidobacterium bifidum* was observed in both strains, identifying both strains belonging to *Bifidobacterium bifidum* (FIG. 1).

```
BiBIF-1
5'-CCACATGATCGCATGTGATTG-3'    (SEQ ID NO: 1)

BiBIF-2
5'-CCGAAGGCTTGCTCCCAAA-3'      (SEQ ID NO: 2)
```

(2) Discrimination of the Strains by Random Amplified Polymorphic DNA (RAPD)

Using as templates the DNA extracted in the same manner as above, the respective organisms were compared by use of 6 members of primers (Nuc. Acid. Res 20, 5137-5142 (1992)). Since YIT 4007 and YIT 10347 show the same band pattern in all of the primers, it was suggested that both strains are genetically closely related. FIG. 2 shows the band patterns of the primers A and E which show a diversity of band patterns.

```
Primer A (SEQ ID NO: 3):    CCGCAGCCAA

Primer B (SEQ ID NO: 4):    AACGCGCAAC

Primer C (SEQ ID NO: 5):    GCGGAAATAG

Primer D (SEQ ID NO: 6):    GAGGACAAAG

Primer E (SEQ ID NO: 7):    CGAACTACAC

Primer F (SEQ ID NO: 8):    GTAGACAAGC
```

(3) Discrimination of the Strains by DNA Polymorphism Analysis with a Restriction Enzyme (RFLP: Restriction Fragment Length Polymorphisms)

Agarose block prepared by mixing culture broths of both strains with low melting point agarose (LMP agarose: made by BIO-RAD) was lysed with lysozyme, and after deproteinization with a proteolytic solution (Proteinase K), washed with a washing buffer (20 mM Tris, 50 mM EDTA). Subsequently, 60 units of each restriction enzyme of XbaI (recognition sequence: T↓CTAGA), Hind III (recognition sequence: AA↓GCTT) and Vsp I (recognition sequence: AT↓TAAT) (all made by Takara) was added to the agarose block, allowed to stand overnight at 4° C., and then allowed to react for enzyme treatment at 37° C. for 24 hours. After treatment with enzymes, the product was subjected to pulse field electrophoresis on 1 mass % agarose gel (PFC Agarose; made by BIO-RAD) using CHEF MAPPER (made by BIO-RAD). After electrophoresis, the gel was stained with 0.5 mg/L of ethylene bromide solution for 30 minutes, then decolorized with distilled water for 30 minutes, and photographed under ultraviolet ray to analyze with the naked eye. In all of the restriction enzymes, the results of the RFLP analysis on both strains were completely identical (FIG. 3).

EXAMPLE 3

Test for Confirmation of the Survivability

Using *Bifidobacterium bifidum* YIT 10347 and YIT 4007, fermented milk drinks or foods were prepared as follows. That is, the above *Bifidobacterium bifidum* strains were respectively inoculated in an amount of 2 mass % on skim milk containing 14 mass % fat-free milk solid portion and incubated at 37° C. up to pH 4.8, and then homogenized at 15 MPa to give a cell solution A. On the other hand, *Streptococcus thermophilus* was inoculated by 0.1 mass % on skim milk containing 14 mass % fat-free milk solid portion, incubated at 37° C. up to pH 4.3, and homogenized at 15 MPa to give a cell solution B. Subsequently, a syrup solution containing sucrose was prepared so that the final concentration of the mixture became 4 mass %. The cell solution A, the cell solution B and the syrup solution were mixed at the ratio of 55:3:42 to prepare fermented milk containing 8.1 mass % fat-free milk solid portion.

The fermented milk (100 mL each) prepared as above was placed in a 100 mL volume oxygen impermeable paper-aluminum combined vessel (surface area 143 $cm^2$; oxygen permeability (per vessel) 0 mL/24 h atm, 25° C.) and an oxygen-permeable polystyrene vessel (surface area 125.6 $cm^2$; oxygen permeability (per vessel) 2.1 mL/24 h atm, 25° C.), respectively, and preserved at 10° C. for 14 days. The cell number immediately after preparation and after storage was counted, respectively, to compare the survivability of *Bifidobacterium bifidum*. In this test, the paper-aluminum combined vessel corresponds to storage under anaerobic condition and the polystyrene vessel corresponds to storage under aerobic condition.

The results indicated that the survival rate of YIT 4007 in the oxygen permeable polystyrene vessel was 2%, but that of YIT 10347 strain in the oxygen permeable polystyrene vessel was 34%, indicating that YIT 10347 has a higher survival rate than YIT 4007 (Table 4).

TABLE 4

| | | Cell number (CFU/mL) | | |
|---|---|---|---|---|
| Strain | Vessel | Immediately after preparation | After 14 days | Survival rate (%) |
| YIT 4007 | Pap-Al com. | $1.5 \times 10^9$ | $5.7 \times 10^8$ | 38 |
| | Polystyrene | $1.3 \times 10^9$ | $2.6 \times 10^7$ | 2 |
| YIT 10347 | Pap-Al com. | $1.9 \times 10^9$ | $1.0 \times 10^9$ | 53 |
| | Polystyrene | $2.0 \times 10^9$ | $6.8 \times 10^8$ | 34 |

EXAMPLE 4

Test for Confirmation of the Change of Character

Using *Bifidobacterium bifidum* YIT 10347 and YIT 4007 strains, respectively, fermented milk drinks or foods were prepared as follows. That is, the above YIT 10347 and YIT 4007 strains were respectively inoculated in an amount of 2 mass % on skim milk containing 14 mass % fat-free milk solid portion and incubated at 37° C. up to pH 4.8, and then homogenized at MPa to give a cell solution A. On the other hand, *Streptococcus thermophilus* was inoculated by 0.1 mass % on skim milk containing 14 mass % fat-free milk solid portion, incubated at 37° C. up to pH 4.3, and homogenized at 15 MPa to give a cell solution B. Subsequently, a syrup solution containing sucrose (final concentration: 4.2 mass %) or isoglucose (final concentration: 5.6 mass %) as sweetener was prepared. The cell solution A, the cell solution B and the syrup solution were mixed in the ratio of 55:3:42 to prepare a fermented milk drink or food containing 8.1 mass % fat-free milk solid portion.

The above prepared fermented milk drink or food (100 mL) was placed in the same polystyrene vessel as in Example 1, and stored at 20° C. for 4 days (under aerobic condition). Immediately after preparation and after storage, the acidity and pH were measured and the taste was evaluated by 10 subjects. In this test, the criteria for evaluation of the taste was as follows.

The results indicated that when sucrose was used as a sweetener, YIT 10347 strain showed a smaller change in acidity than YIT 4007 strain even after storage at 20° C. for 4 days, and the taste was also better because the smell of acetic acid and fermentation was weaker. On the other hand, when isoglucose was used as a sweetener, there was no difference between YIT 4007 and YIT 10347 strains in the change of acidity and taste after storage at 20° C. for 4 days (Table 5 and Table 6).

<Criteria for Evaluation of the Taste>
(Score) (Evaluation)
+2: very good taste
+1: good taste
±0: no preference
−1: dissatisfactory taste
−2: bad taste

TABLE 5

| Sweetener | Strain | Acidity | | pH | |
|---|---|---|---|---|---|
| | | Immediately after preparation | After storage | Immediately after preparation | After storage |
| Sucrose | YIT10347 | 5.5 | 6.2 | 4.89 | 4.88 |
| | YIT4007 | 5.6 | 7.7 | 4.81 | 4.66 |
| Isoglucose | YIT10347 | 5.5 | 7.5 | 4.87 | 4.70 |
| | YIT4007 | 5.6 | 7.3 | 4.84 | 4.71 |

TABLE 6

| Sweetener | Strain | Taste (Average) | | |
|---|---|---|---|---|
| | | Immediately after preparation | After storage | Free description After storage |
| Sucrose | YIT10347 | 0.88 | 0.28 | mild, less AcOH smell, milky |
| | YIT4007 | 0.90 | −0.15 | strong ferm./AcOH smell, strong sourness |
| Isoglucose | YIT10347 | 0.70 | −0.03 | sourness, sharp |
| | YIT4007 | 0.75 | 0.03 | mild sourness, vivid, sharp |

EXAMPLE 5

Preparation of Lactic Acid Bacteria Beverage

Whole milk powder (70 g) and milk peptide (0.1 g) were dissolved in 290 g of water and sterilized at 135° C. for 3 seconds, on which 2 mass % of Bifidobacterium bifidum YIT 10347 was inoculated, and incubated at 37° C. up to pH 4.8, and homogenized at 15 MPa to give 360 g of a cell solution A. On the other hand, 6 g of skim milk was dissolved in 24 g of water and sterilized at 120° C. for 3 seconds, on which 0.1 mass % Streptococcus thermophilus YIT 2021 was inoculated, incubated at 37° C. up to pH 4.3, and homogenized at 15 MPa to give 30 g of a cell solution B. Further, sucrose (50 g), carboxymethylcellulos (5 g), gellan gum (1 g), suclarose (0.1 g), DL-malic acid (0.5 g) and flavor (1 g) were dissolved in water, to which water was added to make the total 610 g; this was sterilized at 120° C. for 3 seconds to give a syrup solution. The cell solution A, the cell solution B and the syrup solution were mixed and put in a 100 mL volume ethylene vinyl alcohol-low density polyethylene combined vessel (ethylene vinyl alcohol surface area 125.6 cm$^2$, the surface of low density polyethylene lid portion 20.9 cm$^2$; the amount of oxygen permeating (per vessel) 0.23 mL/24 h atm, 25° C.) to give a lactic acid bacteria beverage containing 5.5 mass % fat-free milk solid portion. The initial cell number of YIT 10347 in the lactic acid bacteria beverage was 1.3×10$^9$ CFU/mL.

When this lactic acid bacteria beverage was stored at 10° C. for 14 days, the survival rate of YIT 10347 was 14% and the taste was favorable. Further, when it was stored at 20° C. for 4 days, the change of acidity was as small as 0.6, and no deterioration of the taste was recognized.

EXAMPLE 6

Preparation of Fermented Milk

Skim milk (80 g) was dissolved in 470 g of water and sterilized at 135° C. for 3 seconds, on which 2 mass % Bifidobacterium bifidum YIT 10347 was inoculated, incubated at 37° C. up to pH 4.8, and homogenized at 15 MPa to give 550 g of a cell solution A. On the other hand, 5 g of skim milk was dissolved in 25 g of water and sterilized at 120° C. for 3 seconds, on which 0.1 mass % Streptococcus thermophilus YIT 2021 was inoculated, incubated at 37° C. up to pH 4.3, and homogenized at 15 MPa to give 30 g of a cell solution B. Further, 60 g of isoglucose and 5 g of carboxymethylcellulose were dissolved in water, to which 1 g of flavor was added, the mixture was further added with water so that the mixture became the total 420 g. Then the mixture was sterilized at 120° C. for 3 seconds to give a syrup solution. The cell solution A, the cell solution B and the syrup solution were mixed, and placed in the same polystyrene vessel as in Example 1 to give fermented milk containing 8.1 mass % fat-free milk solid portion. The initial cell number of YIT 10347 in the fermented milk was 2.6×10$^9$ CFU/mL.

When this fermented milk was stored at 10° C. for 14 days, the survival rate of YIT 10347 was 35% and the taste was favorable. Further, when it was stored at 20° C. for 4 days, the change of acidity was as small as 0.7, and no deterioration of the taste was recognized.

TEST EXAMPLE 1

Test for Adhesion to the Human Gastric Cells

Bifidobacterium bifidum YIT 10347 or YIT 4007 was inoculated on a GAM bouillon medium (product of Nissui Seiyaku) and incubated at 37° C. for 20 hours anaerobic condition. The culture broth was centrifuged at 3,000 rpm for 10 minutes, and the precipitated cells were washed twice with a phosphate buffered physiological saline (PBS) and suspended in RPMI 1640 (made by Gibco; no fetal bovine serum (FBS); no antibiotic) to prepare a cell suspension. Streptococcus thermophilus YIT 2021 (FERM BP-7537) used as a negative control was inoculated on an MRS medium (made by Difco), incubated in the same manner and suspended to give a suspension of the cells. Further, Lactobacillus gasseri (commercially available isolate) was isolated from commercially available yoghurt (Meiji Probioyoghurt LG21; Meiji Milk Products Co., Ltd.), inoculated on an MILS medium (Iwata & Morishita, Letter in Applied Microbiology, vol. 9, 165-168, 1989), incubated in the same manner, and suspended to give a suspension of the cells. As for Lactobacillus gasseri, adhesiveness to the human gastric cell and eradication of Helicobacter pylori have been reported.

The cell strain derived from the human stomach (GCIY strain; available from the Bioresource Center, Institute of Physical and Chemical Research) was incubated on 15 vol % FBS eagle's MEM medium (containing no antibiotic) on a 24-well collagen coated plate (Sumitomo Bakelite Co., Ltd.) in a carbon dioxide incubator fixed at 37° C. up to a semi-confluent state. The average cell number of the GCIY was 6.53×10$^4$ cells/well. Each well was washed with the above-mentioned RPMI 1640, to which the above-prepared suspension of each strain was added, and this was incubated for 90 minutes and further washed twice with the above RPMI 1640 to remove the non-adhered cells. Thus treated GCIY cells were released with 0.25 w/v % trypsin-1 mM EDTA solution, properly diluted with 0.1 w/v % yeast extract solution, and smeared on a selection medium for each strain (Bifidobacterium bifidum: TOS propionic acid agar medium (Yakult Pharmaceutical Industry Co., Ltd.); *Streptococcus thermophilus, Lactobacillus gasseri*: agar MRS medium (Difco)); thus, the number of the cells adhering to the GCIY strain was calculated from the colony number (FIG. 4).

The adhesiveness of *Bifidobacterium bifidum* YIT 10347 and YIT 4007 to the GCIY strain was compared with that of *Streptococcus thermophilus* as a negative control, indicating that the number of the adhered cells was approximately the same 10 times in both strains. Thus, the adhesiveness was considered to be equivalent in both strains. It was also found that the adhered cell number in both strains was slightly larger than that of a commercially available isolate, *Lactobacillus gasseri* as a positive control.

TEST EXAMPLE 2

Test of the Inhibition for Adhesion of *Helicobacter pylori* to the Human Gastric Cells Experiment A A Pre-incubation System for Bifidus Bacterium and the Cell Strain GCIY Derived from the Human Stomach The cell strain GCIY derived from the human stomach was incubated on a 15 vol % FBS Leibovitz's L-15 medium on a 96-well collagen coated plate in a carbon dioxide incubator fixed at 37° C. up to a semi-confluent state under shading for 2-5 days. Each test strain incubated in the same manner as in Experiment 1 was suspended in a phosphate buffer (PBS) (final concentration $10^8$-$10^9$ CFU/mL) and added into each well, and pre-incubated at 37° C. for 2 hours. Meanwhile, *Helicobacter pylori* was incubated at 37° C. for 40 hours under microaerophilic condition (5% oxygen, 10% carbon dioxide, 85% nitrogen) on a 10 vol % equine serum *Brucella* medium (made by Becton Dickinson) which had been washed once with 20 mM HEPES Leibovitz's L-15 medium (containing no FBS). The *Helicobacter pylori* solution (final concentration $10^7$ CFU/mL) was added to each well, incubated at 37° C. for 90 minutes, washed with PBS, added with 8 w/v % paraformaldeyde solution, and allowed to stand at 4° C. overnight. This was further washed twice with PBS, added with 1 w/v % hydrogen peroxide/methanol solution, allowed to stand at room temperature for 10 minutes, and washed; then, an anti-*Helicobacter pylori* antibody (Anti H.p. (Murine IgG1): Cat. #2007; made by SYNBIO) (100 μl) diluted 200 times with 0.25 w/v % BSA (bovine serum albumin)/PBS was added and incubated at 37° C. for 2 hours. After washing, an anti-mouse IgG antibody (peroxidase-conjugated; made by Cappel) (100 μl) diluted 1,000 times with 0.25 w/v % bovine serum albumin (BSA) PBS was added, and incubated at 37° C. for 1 hour. After washing, a coloring reaction was performed with ABTS coloring reagent, and the reaction was terminated with 1 w/v % sodium dodecylsulfate (SDS), and absorbance was measured at 405 nm. The inhibitory rate (%) for adhesion of *Helicobacter pylori* to the GCIY strain was calculated according to the following equation (FIG. 5).

Inhibitory rate (%)=$(1-A/B)\times 100$

A: Absorbance at the time of addition of the suspension of each test cell strain B: Absorbance in the case of no addition of the suspension of each test cell strain As a result, it was found that when YIT 10347 and YIT 4007 had been allowed to act on the GCIY strain in advance, adhesion of *Helicobacter pylori* added later was inhibited. In particular, the inhibitory activity of YIT 10347 was approximately 6 times as potent as *Streptococcus thermophilus* YIT 2021 as a negative control, and further more potent than *Lactobacillus gasseri* (commercially available isolate) as a positive control. These results suggest that YIT 10347 similarly to the parent strain YIT4007 has a preventive effect against infection or reinfection with *Helicobacter pylori*.

Experiment B

Pre-incubation System for the Bifidus Bacterium and *Helicobacter pylori*

A *Helicobacter pylori* solution ($10^7$ CFU/mL) and PBS suspensions of each test cell strain (final concentration: $10^8$-$10^9$ CFU/mL) prepared in the same manner as in Experiment A were pre-incubated at 37° C. on a 20 mM HEPES Leibovitz's L-15 medium (no addition of FBS) for 2 hours. On the other hand, the cell strain GCIY derived from the human stomach was incubated in the same manner as in Experiment A up to a semi-confluent state and washed once with the above Leibovitz's L-15 medium. To these wells was added the above-described pre-incubated solution, and the wells were incubated at 37° C. for 90 minutes, washed with PBS, added 8 w/v % paraformaldehyde solution, and allowed to stand at 4° C. overnight. The operation hereinafter was conducted in the same manner as in Experiment A, and the adhesion inhibitory rate (%) for adhesion of *Helicobacter pylori* to the GCIY strain was calculated (FIG. 6).

As a result, it was found that when YIT 10347 and YIT 4007 had been allowed to coexist with *Helicobacter pylori* in advance, adhesion of *Helicobacter pylori* to the GCIY strain was inhibited. This indicates that YIT 10347 and YIT 4007 act directly on *Helicobacter pylori* to inhibit the infectivity. The inhibitory activity of YIT 10347 was approximately 3 times as potent as *Streptococcus thermophilus* YIT 2021 as a negative control, and the commercially available isolate *L. gasseri* as a positive control showed approximately the same inhibitory rate as the negative control YIT 2021. These results suggest that YIT 10347 similarly to the parent strain YIT 4007 has an effect of suppressing the activity or effect of *Helicobacter pylori* in a state of infection with *Helicobacter pylori*.

TEST EXAMPLE 3

Test for the Inhibitory Effect of *Bifidobacterium bifidum* YIT 10347 Against IL-8 Derived from the Human Gastric Cell by Infection with *Helicobacter pylori*

*fidobacterium bifidum* YIT 10347 was inoculated on an MILS medium and incubated anaerobically at 37° C. for 20 hours. The culture broth was centrifuged at 5,000 rpm for 5 minutes to collect the cells, which were washed 3 times with 15 vol % FBS eagle's MEM medium (containing no antibiotic) and suspended in a small amount of 15 vol % FBS eagle's MEM medium (containing no antibiotic). On the other hand, the cell strain GCIY derived from the human stomach was incubated on 15 vol % FBS eagle's MEM medium (containing no antibiotic) in a 96-well collagen coated microplate in a carbon dioxide incubator at 37° C. up to a confluent state ($1$-$2\times10^5$ cells/cm$^2$). The culture medium in the wells was removed and replaced with fresh one, and the above YIT 10347 suspension was added on the GCIY cells so that the final concentration became $10^7$ CFU/mL or $10^8$ CFU/mL, and further incubated for 6 hours (pre-incubation). In this connection, the cells pre-incubated only on the culture medium were used as control. The medium in the well was removed, and the well was washed 3 times with PBS to remove YIT 10347; *Helicobacter pylori* was added or not added in the final concentration of $10^7$ CFU/mL together with fresh medium, and the GCIY cells were incubated for 24 hours. After completion of the incubation, the culture supernatant was collected from the well, and IL-8 in the supernatant was determined by ELISA (FIG. 7).

The results indicated as shown in FIG. 7 that in the cell pre-incubated together with YIT 10347, the amount of IL-8 induced by infection with *Helicobacter pylori* was decreased in comparison with the control pre-incubated only in the culture medium. The rate of decrease in the amount of IL-8 was 17% in the case of pre-incubation with addition of 10 CFU/mL and 38% in the case of adding $10^8$ CFU/mL. From this result, it was suggested that YIT 10347 has an effect of inhibiting the production of a leukocyte migration factor IL-8 induced from the gastric epithelial cell by infection with *Helicobacter pylori* and thus could improve inflammation in the stomach caused by infection with *Helicobacter pylori*. It was also suggested that the inhibitory effect became high with increase of the live cell number.

TEST EXAMPLE 4

Test for the Inhibitory Effect of *Bifidobacterium bifidum* YIT 10347 Against IL-8 Induced from the Human Gastric Cell by Addition of TNF-α

*Bifidobacterium bifidum* YIT 10347 was inoculated on an MILS medium and incubated anaerobically at 37° C. for 20 hours. The culture broth was centrifuged at 5,000 rpm for 5 minutes to collect the cells, which were washed 3 times with 15 vol % FBS eagle's MEM medium (containing no antibiotic) and suspended in a small amount of 15 vol % FBS eagle's MEM medium (containing no antibiotic). On the other hand, the cell strain GCIY derived from the human stomach was incubated on 15 vol % FBS eagle's MEM medium (containing no antibiotic) in a 96-well collagen coated microplate in a carbon dioxide incubator at 37° C. up to a confluent state ($1-2\times10^5$ cells/cm$^2$). The culture medium in the wells was removed and replaced with fresh one, and the above YIT 10347 suspension was added on the GCIY cells so that the final concentration became $10^7$ CFU/mL or $10^8$ CFU/mL, and further incubated for 6 hours (pre-incubation). In this connection, the cells pre-incubated only on the culture medium were used as control. The medium in the well was removed, and the well was washed 3 times with PBS to remove YIT 10347; TNF-α was added in the final concentration of 10 ng/mL together with fresh medium, and the GCIY cells were incubated for 24 hours. After completion of the incubation, the culture supernatant was collected from the well, and IL-8 in the supernatant was determined by ELISA (FIG. 8).

The results indicated as shown in FIG. 8 that in the GCIY cell pre-incubated together with YIT 10347, the amount of IL-8 induced by subsequent treatment with TNF-α was decreased in comparison with the control pre-incubated only in the culture medium. The rate of decrease in the amount of IL-8 was 36% in the case of pre-incubation with addition of $10^7$ CFU/mL and 40% in the case of pre-incubation with addition of $10^8$ CFU/mL. From this result, it was found that YIT 10347 has an effect of inhibiting the production of a leukocyte migration factor IL-8 induced by TNF-α which is a mediator of inflammatory reaction. That is, it was suggested that YIT 10347 could improve a variety of inflammation in which TNF-α was involved.

TEST EXAMPLE 5

Test for an Inhibitory Effect of *Bifidobacterium bifidum* YIT 10347 on *Helicobacter pylori* in a Culture Medium

*Helicobacter pylori* ($1\times10^5$ CFU/mL) and *Bifidobacterium bifidum* YIT 10347 ($1\times10^7$ CFU/mL) both were inoculated on a 10 vol % equine serum *Brucella* broth adjusted at pH 5.8 with hydrochloric acid, and incubated in a microaerophilic condition at 37° C. with shaking. A portion was taken out from the culture broth in the mixing culture with a lapse of time and smeared on plates of a *Helicobacter* agar medium (Nissui Seiyaku) and of TOS propionic acid agar medium (Yakult Pharmaceutical Industry Co., Ltd.), respectively. The former was incubated in a microaerobic condition at 37° C. for 5 days, and the latter anaerobically at 37° C. for 3 days to grow colonies, from which the live cell number in both organisms was determined. As for a control, *Helicobacter pylori* was inoculated alone and the live cell number was counted (FIG. 9).

The results indicated as shown in FIG. 9 that in a control of *Helicobacter pylori* alone, *Helicobacter pylori* was grown up to $1\times10^7$ CFU/mL after the lapse of 48 hours. In the case of coexistence of YIT 10347, the live cell number of *Helicobacter pylori* decreased with the lapse of time and was reduced to under $1\times10^3$ CFU/mL after 48 hours. At this stage, the live cell number of YIT 10347 was increased 10 times or more compared with the inoculation stage. From these results, it was found that the growth of *Helicobacter pylori* was inhibited by YIT 10347 in the presence of the live cells of YIT 10347. That is, it is considered that the live strain YIT 10347 ingested by a person would inhibit the growth of *Helicobacter pylori* in the stomach.

TEST EXAMPLE 6

Comparative Test of the Inhibitory Effects of *Bifidobacterium bifidum* YIT 10347 and YIT 4007 for IL-8 Induced from the Human Gastric Cells by Infection with *Helicobacter pylori*

*Bifidobacterium bifidum* YIT 10347 or YIT 4007 was inoculated on an MILS medium and incubated anaerobically at 37° C. for 20 hours. The culture broth was centrifuged at 5,000 rpm for 5 minutes to collect the cells, which were washed 3 times with 15 vol % FBS eagle's MEM medium (containing no antibiotic substance) and suspended in a small amount of 15 vol % FBS eagle's MEM medium (containing no antibiotic substance). On the other hand, the cell strain GCIY derived from the human stomach was incubated on 15 vol % FBS eagle's MEM medium (containing no antibiotic) in a 96-well collagen coated microplate in a carbon dioxide incubator at 37° C. up to a confluent state ($1-2\times10^5$ cells/cm$^2$). The culture medium in the wells was removed and replaced with fresh one, and the above YIT 10347 or YIT 4007 suspension was added on the GCIY cells so that the final concentration became $10^6$ CFU/mL, and further incubated for 6 hours (pre-incubation). In this connection, the cells pre-incubated only on the culture medium were used as control. The medium in the well was removed, and the well was washed 3 times with PBS to remove the cells of *Bifidobacterium bifidum*; then, *Helicobacter pylori* was added or not added in the final concentration of $10^7$ CFU/mL together with fresh medium, and the GCIY cells were incubated for 24 hours. After completion of the incubation, the culture supernatant was collected from the well, and IL-8 in the supernatant was determined by ELISA (FIG. 10).

From the results as shown in FIG. 10, it is indicated that in the cell pre-incubated together with YIT 10347 or YIT 4007, the amount of IL-8 induced by infection with *Helicobacter pylori* was decreased in comparison with the control pre-incubated only in the culture medium. The rate of decrease in the amount of IL-8 was 7% in the case of pre-incubation with addition of YIT 4007, but as high as 28% in the case of pre-incubation with addition of YIT 10347. From this result, it was shown that YIT 10347 and YIT 4007 have an effect of inhibiting the production of a leukocyte migration factor IL-8 induced from the gastric epithelial cell by infection with *Helicobacter pylori*, and the inhibitory effect of YIT 10347 is higher than that of YIT 4007.

TEST EXAMPLE 7

Comparative Test of the Inhibitory Effects of *Bifidobacterium bifidum* YIT 10347 and YIT 4007 for IL-8 Induced from the Human Gastric Cell by Addition of TNF-α

*Bifidobacterium bifidum* YIT 10347 or YIT 4007 was inoculated on an MILS medium and incubated anaerobically at 37° C. for 20 hours. The culture broth was centrifuged at 5,000 rpm for 5 minutes to collect the cells, which were washed 3 times with 15 vol % FBS eagle's MEM medium (containing no antibiotic) and suspended in a small amount of 15 vol % FBS eagle's MEM medium (containing no antibiotic). On the other hand, the cell strain GCIY derived from the human stomach was incubated on 15 vol % FBS eagle's MEM medium (containing no antibiotic) in a 96-well collagen coated microplate in a carbon dioxide incubator at 37° C. to be brought up to a confluent state (1 to $2 \times 10^5$ cells/cm$^2$). The culture medium in the wells was removed and replaced with fresh one, and the above YIT 10347 or YIT 4007 suspension was added on the GCIY cells so that the final concentration became $10^6$ CFU/mL, and further incubated for 6 hours (pre-incubation). In this connection, the cells pre-incubated only on the culture medium were used as control. The medium in the well was removed, and the well was washed 3 times with PBS to remove the cells of *Bifidobacterium bifidum*; TNF-α was added in the final concentration of 10 ng/mL together with fresh medium, and the GCIY cells were incubated for 24 hours. After completion of the incubation, the culture supernatant was collected from the well, and IL-8 in the supernatant was determined by ELISA (FIG. 11).

From the results as shown in FIG. 11, it is indicated that in the GCIY cell pre-incubated together with YIT 10347 or YIT 4007, the amount of IL-8 induced by subsequent treatment with TNF-α was decreased in comparison with the control pre-incubated only in the culture medium. The rate of decrease in the amount of IL-8 was 1% in the case of YIT 4007, but 15% in the case of pre-incubation with addition of YIT 10347. From this result, it was shown that YIT 10347 and YIT 4007 have an effect of inhibiting the production of a leukocyte migration factor IL-8 induced by TNF-α which is a mediator of inflammatory reaction, and the inhibitory effect is higher in YIT 10347 than in YIT 4007.

TEST EXAMPLE 8

Test of Administration of a Lactic Acid Bacteria Beverage Containing *Bifidobacterium bifidum* YIT 10347 in Human On 79 healthy adults who were worried about their stomach, a double-blind random comparative test between the parallel two groups using a placebo as control was conducted in the following subjects. On these subjects, the informed consent was obtained from them in advance.

<Subjects>
(1) Healthy adults who are worried about their stomach (excluding pregnant women)
(2) Those whose value in the urea breath test (the $\Delta^{13}CO_2$ value 20 minutes after administration of Ubit; $^{13}C$ urea preparation made by Otsuka Pharmaceutical Co. Ltd.; carried out according to the manual for examination) is 5‰ or higher and whose pepsinogen I/II ratio is less than 6.5
(3) Those who have not ingested any pharmaceutical or food product which may have an influence on the stomach condition
(4) Those who have no milk allergy or lactose intolerance
(5) Those who have no chronic diseases In the test, the food product to be tested (lactic acid bacteria beverage containing *Bifidobacterium bifidum* YIT 10347 prepared in Example 5) or a placebo food (non-fermented milk) was ingested at a dose of one piece (100 mL/piece) once a day at an uprising and hungry time for 12 weeks; the term of observation was 8 weeks after completion of the ingestion. Before ingestion, after 4 weeks during ingestion, after 8 weeks during ingestion, after 12 weeks during ingestion, and 8 weeks after ingestion (on the 20 weeks from the start of test), a physician observed the change of a subjective symptom by interview and measured on the following items.

<Items to be Measured>
(1) Exhalation $\Delta^{13}CO_2$ value by an urea breath test
(2) Serum pepsinogen value
(3) The amount of *Helicobacter pylori* antigen in feces The measurement of the above items (1) to (3) was conducted in BML Co., Ltd.

Analysis of the above test results was made on the whole subjects, *Helicobacter pylori* positive subjects, and the active gastritis group and the borderline group of atrophic gastritis based on grouping by Yoshihara et al. (Estimation of the state of gastric mucosa by the pepsinogen value, the source: Yoshihara et al., Medical Practice, vol. 21, 77-81, 2004); further, comparison between the groups for each measured value (Mann-Whitney test), comparison of the variation from the baseline before and after (Wilcoxon test), and comparison of the improved degree of subjective symptom were made.

(Test Results)

1. Influence on the Gastric State (Secretion of Gastric Acid, Endogastritis)

In the whole subjects or the subjects of the active gastritis group, the pepsinogen I value in the test food product group was significantly lower than that of the placebo (FIG. 12 and FIG. 13). Since the pepsinogen I value correlates with the secretion of gastric acid, these results indicate that a lactic acid bacteria beverage containing YIT 10347 has an effect of suppressing increase of the gastric acid, and further an effect of suppressing the gastric acid in the active gastritis in which an inflammatory reaction is repeated by attack of *Helicobacter pylori*, and a preventive or therapeutic effect for hyperchylia or reflux esophagitis.

In the subjects of the borderline group of atrophic gastritis, the pepsinogen II value in the test food product group was significantly lower than that of the placebo (FIG. 14). Since the pepsinogen II value reflects the inflammation of gastric mucosa, these results indicate that a lactic acid bacteria beverage containing YIT 10347 has an effect of alleviating inflammation of the gastric mucosa including atrophic gastritis. In this connection, since *Streptococcus thermophilus* contained in the test food product has been confirmed no effect on the pepsinogen value, it is considered that the effect observed in the test food product depends on *Bifidobacterium bifidum* YIT 10347.

2. Influence on *Helicobacter pylori* (Bioactivity, Cell Number, the Amount of Cells)

In all of *Helicobacter pylori* positive persons or *Helicobacter pylori* positive subjects of the active gastritis group, the exhalation $\Delta^{13}CO_2$ value in the test food product group was lower than the baseline, and the variation was also lower than the placebo group (FIG. 15, FIG. 16). Since the exhalation $\Delta^{13}CO_2$ value reflect the urease activity essential for the growth and activity of *Helicobacter pylori* in the stomach, these results indicate that a lactic acid bacteria beverage containing YIT 10347 exhibits an anti-*Helicobacter pylori* effect (decrease of the cell number of *Helicobacter pylori*, inhibition of the generation of ammonia by *Helicobacter pylori*, alleviation/prevention/cure of injury of the gastric mucosa by *Helicobacter pylori*, improvement of an inflammatory reaction by *Helicobacter pylori*, and the like) through inhibition of the urease activity (decrease of the amount of ammonia) of *Helicobacter pylori*. In the *Helicobacter pylori* positive subjects of the borderline group of atrophic gastritis, the amount of *Helicobacter pylori* antigen in feces in the test food product group was lower than the baseline (FIG. 17). Since the amount of *Helicobacter pylori* antigen reflects the amount of the cells of *Helicobacter pylori*, these results indicate that a lactic acid bacteria beverage containing YIT 10347 exhibits an effect of decreasing the cell number of *Helicobacter pylori*. In this connection, since *Streptococcus thermophilus* contained in the test food product has been confirmed no effect on *Helicobacter pylori*, it is considered that the effect observed in the test food product depends on *Bifidobacterium bifidum* YIT 10347.

3. Influence on the Gastric Condition

On the change of a subjective symptom by interview to the entire subjects, the rate of improvement of an indefinite complaint (stomach ache, indigestible, heavy in the stomach, retching, unpleasant feel, heartburn, upper bellyache, belch) in the stomach in the test food product group was higher than in the placebo group (FIG. 18). The details are as follows: improvement of stomach ache in the test food product group: 9 subjects, and no improvement: 1 subject (improving rate 90%); improvement in the placebo group: 4 subjects, and no improvement: 2 subjects (improving rate 67%); improvement of indigestible in the test food product group: 4 subjects, and no improvement: 1 subject (improving rate 80%); improvement in the placebo group: 1 subject, and no improvement: 2 subjects (improving rate 33%); and improvement of the other conditions (heavy in the stomach, retching, unpleasant feel, heartburn, upper bellyache, belch) in the test food product group: 3 subjects, and no improvement: none (improving rate 100%); improvement in the placebo group: 5 subjects, and no improvement: 3 subjects (improving rate 63%). These results indicate that a lactic acid bacteria beverage containing YIT 10347 exhibits an effect of improving efficiently indefinite complaint in the stomach. In this connection, since *Streptococcus thermophilus* contained in the test food product has been confirmed no effect on the gastric condition, it is considered that the effect observed in the test food product depends on *Bifidobacterium bifidum* YIT 10347.

INDUSTRIAL APPLICABILITY

*Bifidobacterium bifidum* of the invention has an effect of killing *Helicobacter pylori* and shows high survivability even in the case of being stored in a fermented milk drink or food under aerobic condition. Since the above-mentioned killing effect and the survivability are maintained over a long period of time and a large amount of the living cells can be delivered at the stomach and intestinal tract, it may be utilized as a preventive or therapeutic agent for infection with *Helicobacter pylori*, a preventive or therapeutic agent for gastritis and ulcer, a preventive or therapeutic agent for indefinite complaint in stomach, or a preventive or therapeutic agent for hyperchylia and gastroesophageal reflux. In addition, it can be utilized preferably in production of drinks and foods, particularly fermented milk drinks or foods. Further, since it suppresses increase of the acidity and deterioration of the taste during storage of a fermented milk drink or food in which sucrose is used, it can be utilized preferably in fermented milk drinks and foods containing sweeteners.

BRIEF DESCRIPTION OF DRAWINGS

FIG. 1 shows the result of species identification of YIT 4007 and YIT 10347 using a BiBIF primer.

FIG. 2 shows the RAPD band patterns of YIT 4007 and YIT 10347.

FIG. 3 shows the pulse field electrophoresis patterns of chromosome DNAs of YIT 4007 and YIT 10347.

FIG. 4 shows the results of a test for adhesiveness to the human gastric cell.

FIG. 5 shows the results of an inhibition test for the adhesion of *Helicobacter pylori* to the gastric cell.

FIG. 6 shows the results of an inhibition test for the adhesion of *Helicobacter pylori* to the gastric cell.

FIG. 7 shows the test results of an inhibitory effect of YIT 10347 for IL-8 induced from the human gastric cells by infection with *Helicobacter pylori*.

FIG. 8 shows the test results of an inhibitory effect of YIT 10347 for IL-8 induced from the human gastric cells by addition of TNF-α.

FIG. 9 shows the test results of an inhibitory effect for *Helicobacter pylori* by YIT 10347 in the culture broth (Experiment A: culture by a single bacterium; Experiment B: mixing culture).

FIG. 10 shows the results of a comparison test of an inhibitory effect of YIT 10347 and YIT 4007 to IL-8 induced from the human gastric cells by infection with *Helicobacter pylori*.

FIG. 11 shows the results of a comparison test of an inhibitory effect of YIT 10347 and YIT 4007 to IL-8 induced from the human gastric cells by addition of TNF-α.

FIG. 12 shows the results (the pepsinogen I value in the whole subjects) of an administration test of a lactic acid bacteria beverage containing YIT 10347 in human.

FIG. 13 shows the results (the pepsinogen I value in the subjects of active gastritis) of an administration test of a lactic acid bacteria beverage containing YIT 10347 in human.

FIG. 14 shows the results (the pepsinogen II value in the subjects of the borderline group of atrophic gastritis) of an administration test of a lactic acid bacteria beverage containing YIT 10347 in human.

FIG. 15 shows the results (the exhalation $\Delta^{13} CO_2$ value in the entire subjects positive to *Helicobacter pylori*) of an administration test of a lactic acid bacteria beverage containing YIT 10347 in human.

FIG. 16 shows the results (the exhalation $\Delta^{13} CO_2$ value in the active gastritis subjects positive to *Helicobacter pylori*) of an administration test of a lactic acid bacteria beverage containing YIT 10347 in human.

FIG. 17 shows the results (the amount of *Helicobacter pylori* antigen in the feces of the subjects of the borderline group of atrophic gastritis and positive to *Helicobacter pylori*) of an administration test of a lactic acid bacteria beverage containing YIT 10347 in human.

FIG. 18 shows the results (the rate of improvement of indefinite complaint in the stomach in the entire subjects) of an administration test of a lactic acid bacteria beverage containing YIT 10347 in human.

The invention claimed is:

1. An biologically pure culture of *Bifidobacterium bifidum* YIT 10347 (FERM BP-10613).

2. A drink or food comprising the biologically pure culture of *Bifidobacterium bifidum* YIT 10347 (FERM BP-10613) as claimed in claim 1 in an amount of $10^5$-$10^{13}$ viable cells.

3. The drink or food as claimed in claim 2, which is a fermented milk drink or food.

4. The drink or food as claimed in claim 2 or 3, further comprising a sweetener.

5. A package, comprising the drink or food as claimed in claim 2 contained in a vessel.

6. The package as claimed in claim 5, wherein the vessel comprises an oxygen permeable wrapping material.

7. A method for treating a *Helicobacter pylori* infection, the method comprising administering to a subject in need thereof an effective amount of a composition comprising, as an active ingredient the biologically pure culture of *Bifidobacterium bifidum* YIT 10347 (FERM BP-10613) as claimed in claim 1.

* * * * *